US007968582B2

(12) United States Patent
Cuberes

(10) Patent No.: US 7,968,582 B2
(45) Date of Patent: *Jun. 28, 2011

(54) 5(S)-SUBSTITUTED PYRAZOLINE COMPOUNDS, THEIR PREPARATION AND USE AS MEDICAMENTS

(75) Inventor: Rosa Cuberes, Barcelona (ES)

(73) Assignee: Laborotorios Del Dr. Esteve, S.A., Barcelona (ES)

(*) Notice: Subject to any disclaimer, the term of this patent is extended or adjusted under 35 U.S.C. 154(b) by 0 days.
This patent is subject to a terminal disclaimer.

(21) Appl. No.: 11/457,727

(22) Filed: Jul. 14, 2006

(65) Prior Publication Data

US 2007/0015811 A1    Jan. 18, 2007

Related U.S. Application Data

(60) Provisional application No. 60/705,482, filed on Aug. 5, 2005.

(30) Foreign Application Priority Data

Jul. 15, 2005   (EP) .................................... 05384008

(51) Int. Cl.
   *C07D 231/06*   (2006.01)
   *A01N 43/56*    (2006.01)
(52) U.S. Cl. ..................................... 514/403; 548/379.1
(58) Field of Classification Search .................. None
   See application file for complete search history.

(56) References Cited

U.S. PATENT DOCUMENTS

| | | | |
|---|---|---|---|
| 5,017,596 A | 5/1991 | Colombo et al. | |
| 5,624,941 A | 4/1997 | Barth et al. | |
| 5,849,931 A | 12/1998 | Frigola-Constansa et al. | |
| 6,118,009 A | 9/2000 | Torrens-Jover et al. | |
| 6,187,930 B1 | 2/2001 | Torrens-Jover et al. | |
| 6,410,582 B1 | 6/2002 | Merce-Vidal et al. | |
| 6,476,060 B2 | 11/2002 | Lange et al. | |
| 6,509,367 B1 | 1/2003 | Martin et al. | |
| 6,610,737 B1 | 8/2003 | Garzon et al. | |
| 6,956,033 B2 | 10/2005 | Ogawa et al. | |
| 7,138,424 B2 | 11/2006 | Barth et al. | |
| 2002/0058816 A1 | 5/2002 | Kordik et al. | |
| 2002/0156104 A1 | 10/2002 | Adams et al. | |
| 2003/0022925 A1 | 1/2003 | Merce-Vidal et al. | |
| 2003/0153569 A1 | 8/2003 | Adams et al. | |
| 2004/0092535 A1 | 5/2004 | Barsanti et al. | |
| 2004/0248944 A1 | 12/2004 | Kruse et al. | |
| 2005/0137251 A1 | 6/2005 | Garzon et al. | |
| 2005/0171179 A1 | 8/2005 | Lange et al. | |
| 2005/0222138 A1 | 10/2005 | Ohhata et al. | |
| 2005/0282798 A1 | 12/2005 | Lazzari et al. | |
| 2006/0015198 A1 | 1/2006 | Okabayashi et al. | |
| 2006/0020010 A1 | 1/2006 | Altisen et al. | |
| 2006/0052315 A1 | 3/2006 | Leung et al. | |
| 2006/0106014 A1 | 5/2006 | Boddupalli et al. | |
| 2006/0128673 A1 | 6/2006 | Firnges et al. | |
| 2006/0172019 A1 | 8/2006 | Ralston et al. | |
| 2006/0189658 A1 | 8/2006 | Altisen et al. | |
| 2006/0194843 A1 | 8/2006 | Berdini et al. | |
| 2007/0015810 A1* | 1/2007 | Cuberes .................. | 514/406 |
| 2007/0015811 A1 | 1/2007 | Cuberes | |
| 2007/0021398 A1* | 1/2007 | Torrens et al. .............. | 514/183 |
| 2007/0066651 A1 | 3/2007 | Cuberes-Altisen et al. | |
| 2007/0073056 A1* | 3/2007 | Torrens et al. .............. | 540/575 |
| 2007/0254862 A1* | 11/2007 | Antel et al. ................. | 514/183 |
| 2008/0015198 A1 | 1/2008 | Cuberes-Altisen et al. | |

FOREIGN PATENT DOCUMENTS

| | | |
|---|---|---|
| DE | 3540934 | 5/1987 |
| EP | 1384477 | 1/2004 |
| GB | 1 209 326 | 10/1970 |
| JP | 02 117 605 A | 10/1988 |
| WO | 8805046 A2 | 7/1988 |
| WO | WO 88/05046 A2 | 7/1988 |
| WO | WO 88/06583 | 7/1988 |
| WO | WO 92/03421 | 3/1992 |
| WO | WO 00/76503 A1 | 12/2000 |
| WO | 0170700 | 6/2001 |
| WO | WO 02/080909 A1 | 10/2002 |
| WO | 03026647 | 4/2003 |
| WO | 03097597 A2 | 11/2003 |
| WO | WO 2004/060882 A1 | 7/2004 |
| WO | WO 2004/078261 A1 | 9/2004 |
| WO | 2005012256 | 2/2005 |
| WO | 2006045799 | 5/2006 |
| WO | WO 2006/077414 A1 | 7/2006 |
| WO | WO 2006/077419 A1 | 7/2006 |
| WO | WO 2006/077425 A1 | 7/2006 |
| WO | WO 2006/077428 A1 | 7/2006 |

OTHER PUBLICATIONS http://mojo.calyx.net/~olsen/MEDICAL/IOM/iom115054635.html (25 pages).*
http://www.norml.org/index.cfm?Group_ID=7282&wtm_format=print (2 pages).*
http://www.nlm.nih.gov/medlineplus/ency/article/001553.htm (3 pages).*
http://www.webmd.com/diet/tc/Obesity-Overview (3 pages).*
http://health.yahoo.com/topic/addiction/abuse/article/pt/Psychology_Today_articles_pto_term_alcohol (6 pages).*
Megard et al., "A co-culture based model of human blood-brain barrier: application to active transport of indinavir and in vivo-in vitro correlation", Brain Research, 927, 2002, 153-167.*
Fact sheet Alzheimers association, 2 pages.*
http://www.mayoclinic.com/health/alzheimers-disease/DS00161/DSECTION=3.*
http://www.medindia.net/patients/patientinfo/Alzheimers_treatment.htm.*
Zips et al, "new anticancer agents: in vitro and in vivo", in vivo, 2005, 19, 1-7.*
Chawla et al., "Challenges in Polymorphism of Pharmaceuticals", CRIPS vol. 5, No. 1, Jan.-Mar. 2004 (4 PAGES.*
Newman et al., "Solid-state analysis of the active pharmaceutical ingredient in drug products", DDT vol. 8, No. 19, Oct. 2003, p. 898-905.*

(Continued)

*Primary Examiner* — Sun Jae Y Loewe
(74) *Attorney, Agent, or Firm* — Banner & Witcoff, Ltd.

(57) ABSTRACT

The present invention relates to substituted pyrazoline compounds, methods for their preparation, medicaments comprising these compounds as well as their use for the preparation of a medicament for the treatment of humans and animals.

11 Claims, 1 Drawing Sheet

OTHER PUBLICATIONS

Antel et al., caplus an 2007:1278230.*
Buschman et al., caplus an 2007:175440.*
Buschman et al. 2, caplus an 2007:173847.*
Buschman 3, caplus an 2007:88351.*
http://mojo.calyx.net/~olsen/MEDICAL/IOM/iom115054635.html (25 pages) 2007.*
http://www.norml.org/index.cfm?Group_ID=7282&wtm_format=print (2 pages) 2007.*
http://www.nlm.nih.gov/medlineplus/ency/article/001553.htm (3 pages) 2007.*
http://www.webmd.com/diet/tc/Obesity-Overview (3 pages) 2007.*
http://health.yahoo.com/topic/addiction/abuse/article/pt/Psychology_Today_articles_pto_term_alcohol (6 pages) 2007.*
Fact sheet Alzheimers association, 2 pages 2007.*
http://www.mayoclinic.com/health/alzheimers-disease/DS00161/DSECTION=3 2007.*
http://www.medindia.net/patients/patientinfo/Alzheimers_treatment.htm 2007.*
Chan et al., "N-substituted Pyrazoline-type Insecticides", ACS Symposium Series, No. 800, p. 144-155 (2002); Chem. Abstr. XP002335857.
Meier et al., "Insecticidal Dihydropyrazoles with Reduced Lipophilicity", ACS Symposium Series, No. 504 p. 313-326 (1992); Chem Abstr. XP002335858.
Meyer et al., "1,5-Diaryl-2,3-pyrrolidinediones—Phenylhydrazine Derivatives", Journal of Organic Chemistry, vol. 22: 1565-1567 (1957); Chem Abstr. XP002335859.
International Search Report mailed Jul. 29, 2005 in International Application No. PCT/EP2005/001659.
Kenji Tamura et al., "One-Pot Synthesis of Trifluoroacetimidoyl Halides", J. Org. Chem. 1993, 58, 32-38.
Hollister, L. E., "Health Aspects of Cannabis," Pharmacological Reviews, vol. 38, No. 1, pp. 1-20 (1986).
Murphy, L. et al., Consroe and Sandyk, "Potential Role of Cannabinoids for Therapy of Neurological Disorders," pp. 459-524, CRC Press (1992).
Slavinska, V. et al, "New Way for the Preparation of 4-Phenyl-2-Oxobutyric Acid Ethyl Ester," Synthetic Communications, 26(11), 2229-2233 (1996).
DuJardin, G. et al., "A Straightforward Route to E-γ-Aryl-α-oxobutenoic Esters by One-step Acid-catalysed Crotonisation of Pyruvates," Synlett, No. 1, pp. 147-149 (2001).
Pascual, Alfons, "Synthese des 5-[(Acetylhydrazono)-(4-chlorphenyl)-methyl]thiophen-2-yl-esters der Trifluormethansulfonäure," J. Prakt. Chem. 341, No. 7, pp. 695-700 (1999).
Lin, S. et al., "Regloselective Friedel-Crafts Acylation with Unsymmetrically Substituted Furandicarboxylic Acid Anhydride and Furan Acid Chloride: Syntheses of 4-Substituted 3-Arylcarbonyl-2-Phenylfuran and 3-Substituted 4-Arylcarbonyl-2-Phenylfuran," Heterocycles, vol. 55, No. 2, pp. 265-277 (2001).
Rao, P. D. et al., "Rational Syntheses of Porphyrins Bearing up to Four Different Meso Substituents," J. Org. Chem., 65, pp. 7323-7344 (2000).
Pearson, D.E. and Buehler, C.A., "Friedel-Crafts Acylations with Little or No Catalyst," Synthesis, No. 10: October, pp. 533-542 (1972).
Ross, Ruth A. et al., "Agonist-Inverse agonist characterization at $CB_1$ and $CB_2$ cannabinoid receptors of L-759633, L759656 and AM630," British Journal of Pharmacology 126, pp. 665-672 (1999).
Howlett, A.C. et al., "International Union of Pharmacology XXVII. Classification of Cannabinoid Receptors," Pharmacological Reviews 54:161-202 (2002).
Compton, David R. et al., "In-Vivo Characterization of a Specific Cannabinoid Receptor Antagonist (SR141716A): Inhibition of $\Delta^9$-Tetrahydrocannabinol-Induced Responses and Apparent Agonist Activity," The Journal of Pharmacology and Experimental Therapeutics, vol. 277, No. 2, 277:586-594 (1996).
Woolfe G. et al., "The Evaluation of the Analgesic Action of Pethidine Hydrochloride (Demerol)," The Journal of Pharmacology and Experimental Therapeutics, vol. 80, pp. 300-307 (1944).
Desmedt L.K.C. et al. "Anticonvulsive Properties of Cinnarizine and Flunarizine in Rats and Mice," Arzneim.-Forsch. (Drug Res.) 25, Nr. 9, pp. 1408-1413 (1975).
G. Colombo et al., "Appetite Suppression and Weight Loss after the Cannabinoid Antagonist SR 141716," Life Sciences, vol. 63, No. 8 pp. PL 113-117 (1998).
Alpermann, H.G. et al., "Pharmacological Effects of Hoe 249: A New Potential Antidepressant," Drug Development Research 25:287-282 (1992).
Seth, R. et al., "Chemistry and Pharmacology of Cannabis," Progress in Drug Research, vol. 36:71-115 (1991).
Muccioli, G.G. et al., "CB1 and CB2 cannabinoid receptor antagonists and inverse agonists for obesity, metabolic syndrome and smoking cessation indications," Expert Opinion on Therapeutic Patents, vol. 16, No. 10, pp. 1405-1423 (2006).
Lange, J.H.M. et al., "3,4-diarylpyrozolines as cannabinoid CB SUB 1 receptor antagonists with lower lipophilicity," Bioorganic & Medicinal Chemistry Letters, vol. 15, No. 21, pp. 4794-4798 (2005).
Thomas, B.F. et al., "Long-chain amide analogs of the cannabinoid CB1 receptor antagonist N-(piperidinyl)-5-(4-chlorophenyl)-1-(2,4-dichlorophenyl)-4-methyl-1H-pyrazole-3-carboxamide," Bioorganic & Medicinal Chemistry, vol. 13, No. 18, pp. 5463-5474 (2005).
Hough, L.B. et al. "Inhibition of Improgan Antiociception by the Cannabinoid (CB)(1) Antagonist N-(piperidin-01-yl)-5 (4-chlorophenyl)-1(2,4-dichlorophenyl)-4-methyl-1H-pyarzole-3-carboxamide (SR141716A): Lack of Obligatory Role for Endocannabinoids Acting at CB(1) Receptors" Journal of Pharmacology and Experimental Therapeutics vol. 303, No. 1 pp. 314-322 (2002).
Hurst, Dow P. et al. "N-(piperidin-l-yl)-5-(4-chlorophenyl)-1-(2,4-dichlorophenyl)-4-methyl-1H-pyrazole-3-caboxamide (SR141716A): interaction with LYS 3.28(192) is Crucial for its Inverse Agonism at the Cannabinoid CB1 Receptor" Molecular Pharmacology vol. 62,No. 6 pp. 1274-1287 (2002).
Joong-Youn, Shim et al. Molecular Interaction of the Antagonist N-(piperidin-1-yl)-5-(4-chlorophenyl)-1-(2,4-dicholorophenyl)-4-methyl-1H-pyrazole-3-carboxamide with the CB1 Cannabinoid Receptor: Journal of Medicincal Chemistry, vol. 45 No. 7, pp. 144-1459 (2002).
Lan, R. et al. "Structure-Activity Relationships of Pyrazole Derivatives as Cannabinoid Receptor Antagonists" Journal of Medicinal Chemistry, vol. 42 No. 4, pp. 769-776 (1999).
Megard et al. "A Co-Culture Based Model of Human Blood-Brain Barrier: Application to Active Transport of Indinavire and In-Vivo-in-Vitro Correlation", Brain Research vol. 927 pp. 153-167, (2002).
Meschler, J.P. et al. "Inverse Agonist Properties of N-(piperidin-1-yl)-5-(4-chlorophenyl)-1-(2, dichlorophenyl)-4-methyl-1H-pyrazole-3-carboxamide HC1(SR141716A) and 1-(2-chlorophenyl)-4-cyano-5-(4-methoxyphenyl)-1H-pyrazole-3-carboxylic acid phenlamide (CP 272871) for CB1 Cannabinoid Receptor" Biochemical Pharmacology vol. 60 pp. 1315-1323 (2000).
Wiley, J.L. et al. "Novel Pyralzole Cannabinoids: Insights into CB(1) Receptor Recognition and Activation" Journal of Pharmacology and Experimental Therapeutics, vol. 296, No. 3 pp. 1013-1022 (2001).
Zips et al. "New Anticancer Agents: In-Vitro and In-Vivo" In Vivo vol. 19, pp. 1-7 (2005).
Vippagunta, Sudha R. et al. "Crystalline Solids," Advanced Drug Delivery Reviews 48:3-26 (2001).
Vaughan, Wyman R. "2,3-Pyrrolidinediones, VI. Reactions with Phenyhydrazine," J. Org. Chem. 20(12): 16i19-1626 (1955).

* cited by examiner

5(S)-SUBSTITUTED PYRAZOLINE COMPOUNDS, THEIR PREPARATION AND USE AS MEDICAMENTS

CROSS-REFERENCE TO RELATED APPLICATIONS

This application claims the benefit of priority of U.S. Provisional Patent Application No. 60/705,482, filed Aug. 5, 2005, and European Patent Application No. 05384008.8, filed Jul. 15, 2005, each of which is hereby incorporated by reference in its entirety.

FIELD OF THE INVENTION

The present invention relates to substituted pyrazoline compounds, methods for their preparation, medicaments comprising these compounds as well as their use for the preparation of a medicament for the treatment of humans and animals.

BACKGROUND OF THE INVENTION

Cannabinoids are compounds, which are derived from the cannabis sativa plant which is commonly known as marijuana. The most active chemical compound of the naturally occurring cannabinoids is tetrahydrocannabinol (THC), particularly $\Delta^9$-THC.

These naturally occurring cannabinoids as well as their synthetic analogues promote their physiological effects via binding to specific G-coupled receptors, the so-called cannabinoid-receptors.

At present, two distinct types of receptors that bind both the naturally occurring and synthetic cannabinoids have been identified and cloned. These receptors, which are designated $CB_1$ and $CB_2$ are involved in a variety of physiological or pathophysiological processes in humans and animals, e.g. processes related to the central nervous system, immune system, cardiovascular system, endocrinous system, respiratory system, the gastrointestinal tract or to reproduction, as described for example, in Hollister, Pharm. Rev. 38, 1986, 1-20; Reny and Singha, Prog. Drug. Res., 36, 71-114, 1991; Consroe and Sandyk, in Marijuana/Cannabinoids, Neurobiology and Neurophysiology, 459, Murphy L. and Barthe A. Eds., CRC Press, 1992.

Therefore, compounds, which have a high binding affinity for these cannabinoid receptors and which are suitable for modulating these receptors are useful in the prevention and/or treatment of cannabinoid-receptor related disorders.

In particular, the $CB_1$-Receptor is involved in many different food-intake related disorders such as bulimia or obesity, including obesity associated with type II diabetes (non-insulin-dependent diabetes) and thus, compounds suitable for regulating this receptor may be used in the prophylaxis and/or treatment of these disorders.

SUMMARY OF THE INVENTION

Thus, it was an object of the present invention to provide novel compounds for use as active substances in medicaments. In particular, these active substances should be suitable for the modulation of Cannabinoid receptors, more particularly for the modulation of Cannabinoid 1 ($CB_1$) receptors.

Said object was achieved by providing the substituted pyrazoline compounds of general formula I given below, their stereoisomers, corresponding salts and corresponding solvates thereof.

It has been found that these compounds have a high affinity for cannabinoid receptors, particularly for the $CB_1$-receptor, and that they act as modulators e.g. antagonists, inverse agonists or agonists on these receptors. They are therefore suitable for the prophylaxis and/or treatment of various disorders related to the central nervous system, the immune system, the cardiovascular system, the endocrinous system, the respiratory system, the gastrointestinal tract or reproduction in humans and/or animals, preferably humans including infants, children and grown-ups.

DETAILED DESCRIPTION OF THE INVENTION

Figure 1:
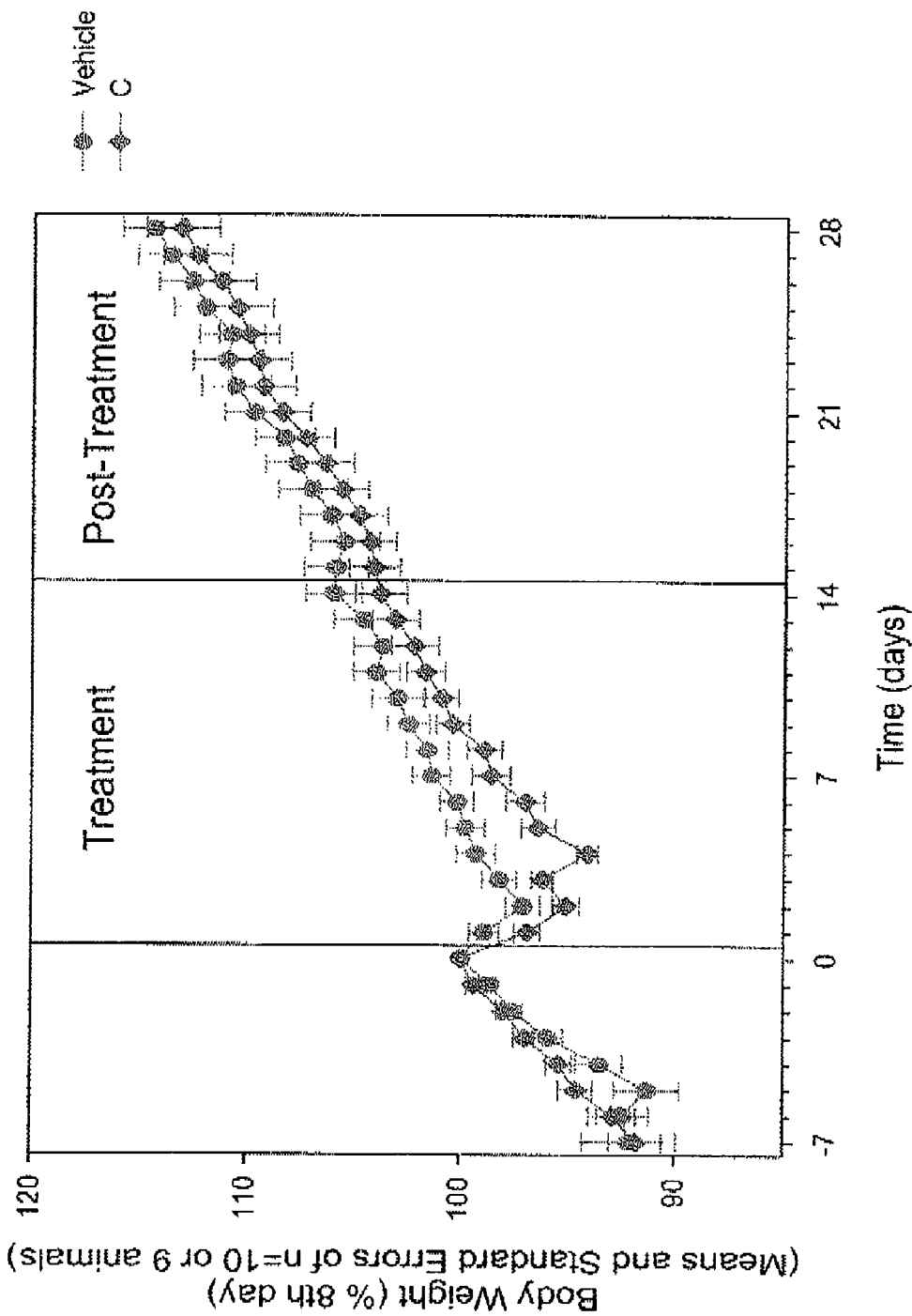
FIG. 1 shows the effect of continued administration (i.p. once daily) of (S)—N-piperidinyl-5-(4-chlorophenyl)-1-(2,4-dichlorophenyl)-4,5-dihydro-1H-pyrazole-3-carboxamide (C) and vehicle on body weight in rats.

Thus, in one of its aspects the present invention relates to substituted pyrazoline compounds of general formula I,

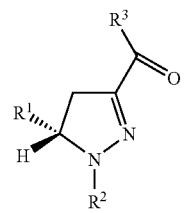

wherein
$R^1$ represents an optionally at least mono-substituted phenyl group,
$R^2$ represents an optionally at least mono-substituted phenyl group,
$R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or $R^3$ represents an optionally at least mono-substituted aryl or heteroaryl group, which may be condensed with an optionally at least mono-substituted mono- or polycyclic ring system, or $R^3$ represents an —$NR^4R^5$-moiety,
$R^4$ and $R^5$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —$SO_2$—$R^6$-moiety, or an —$NR^7R^8$-moiety,
$R^6$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^7$ and $R^8$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of a corresponding N-oxide thereof, or a corresponding salt thereof, or a corresponding solvate thereof, The following provisos (disclaimers) may apply for the pyrazoline compounds of general formula I given above, namely that $R^4$ and $R^5$ do not both represent a hydrogen atom, and/or that if one of the residues $R^4$ and $R^5$ represents a hydrogen atom or an alkyl group, which is optionally at least mono-substituted with an alkoxy group, an alkoxyalkoxy group, a halogen atom or a phenyl group, the other one of these residues $R^4$ and $R^5$ does not represent a pyrid-2-yl group, which is optionally mono-substituted in the 5-position, a pyrid-5-yl group, which is optionally mono-substituted in the 2-position, a pyrimid-5-yl group, which is optionally mono-substituted in the 2-position, a pyridaz-3-yl group, which is optionally mono-substituted in the 6-position, a pyrazin-5-yl group, which is optionally mono-substituted in the 2-position, a thien-2-yl group, which is optionally mono-substituted in the 5 position, a thien-2-yl group, which is optionally at least mono-substituted in the 4-position, a benzyl group, which is optionally mono-substituted in the 4-position of the ring, a phenethyl group, which is optionally mono-substituted in the 4-position of the ring, an optionally mono-, di- or tri-substituted phenyl group, a di-substituted phenyl group, wherein the two substituents together form an $-OCH_2O-$, $-OCH_2CH_2O-$ or $-CH_2CH_2O-$ chain, which is optionally substituted with one or more halogen atoms or one or two methyl groups, an $-NH$-phenyl-moiety, wherein the phenyl group may be mono-substituted in the 4-position, and/or that if one of the residues $R^4$ and $R^5$ represents an alkynyl group, the other one of these residues $R^4$ and R5 does not represent a phenyl group, which is optionally substituted in the 4-position, and/or that if one of the residues $R^4$ and $R^5$ represents a hydrogen atom or a linear or branched, saturated or unsaturated, unsubstituted or substituted aliphatic radical, the other one of these residues $R^4$ and $R^5$ does not represent an unsubstituted or substituted thiazole group or an unsubstituted or substituted [1,3,4]thiadiazole group.

A mono- or polycyclic ring-system according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more, e.g 1, 2 or 3, heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring system are preferably 5- or 6-membered.

The term "condensed" according to the present invention means that a ring or ring-system is attached to another ring or ring-system, whereby the terms "annulated" or "annelated" are also used by those skilled in the art to designate this kind of attachment.

If one or more of the residues $R^3$—$R^8$ represents or comprises a saturated or unsaturated, optionally at least one heteroatom as ring member containing cycloaliphatic group, which is substituted by one or more, e.g. 1, 2, 3 or 4, substituents, unless defined otherwise, each of the substituents may be independently selected from the group consisting of hydroxy, fluorine, chlorine, bromine, branched or unbranched $C_{1-6}$-alkoxy, branched or unbranched $C_{1-6}$-alkyl, branched or unbranched $C_{1-4}$-perfluoroalkoxy, branched or unbranched $C_{1-4}$-perfluoroalkyl, oxo, amino, carboxy, amido, cyano, nitro, $-SO_2NH_2$, $-CO-C_{1-4}$-alkyl, $-SO-C_{1-4}$-alkyl, $-SO_2-C_{1-4}$-alkyl, $-NH-SO_2-C_{1-4}$-alkyl, wherein the $C_{1-4}$-alkyl may in each case be branched or unbranched, and a phenyl group, more preferably be selected from the group consisting of hydroxy, F, Cl, Br, methyl, ethyl, methoxy, ethoxy, oxo, $CF_3$ and a phenyl group.

If one or more of the residues $R^3$—$R^8$ represents or comprises a cycloaliphatic group, which contains one or more heteroatoms as ring members, unless defined otherwise, each of these heteroatoms may preferably be selected from the group consisting of N, O and S. Preferably a cycloaliphatic group may contain 1, 2 or 3 heteroatoms independently selected from the group consisting of N, O and S as ring members.

Suitable saturated or unsaturated, optionally at least one heteroatom as ring member containing, optionally at least mono-substituted cycloaliphatic; groups may preferably be selected from the group consisting of Cyclopropyl, Cyclobutyl, Cyclopentyl, Cyclohexyl, Cycloheptyl, Cyclooctyl, Cyclopentenyl, Cyclohexenyl, Cycloheptenyl, Cyclooctenyl, Pyrrolidinyl, Piperidinyl, Piperazinyl, homo-Piperazinyl and Morpholinyl.

If one or more of the residues $R^3$—$R^8$ comprises a mono- or polycyclic ring system, which is substituted by one or more, e.g. 1, 2, 3, 4 or 5 substituents, unless defined otherwise, each of the substituents may be independently selected from the group consisting of hydroxy, fluorine, chlorine, bromine, branched or unbranched $C_{1-6}$-alkoxy, branched or unbranched $C_{1-6}$-alkyl, branched or unbranched $C_{1-4}$-perfluoroalkoxy, branched or unbranched $C_{1-4}$-perfluoroalkyl, amino, carboxy, oxo, amido, cyano, nitro, $-SO_2NH_2$, $-CO-C_{1-4}$-alkyl, $-SO_2-C_{1-4}$-alkyl, $-SO_2-C_{1-4}$-alkyl, $-NH-SO_2-C_{1-4}$-alkyl, wherein the $C_{1-4}$-alkyl may in each case be branched or unbranched, and a phenyl group, more preferably be selected from the group consisting of hydroxy, F, Cl, Br, methyl, ethyl, methoxy, ethoxy, $CF_3$, oxo and a phenyl group.

If one or more of the residues $R^1$—$R^8$ represents or comprises an aryl group, including a phenyl group, which is substituted by one or more, e.g. 1, 2, 3, 4 or 5 substituents, unless defined otherwise, each of the substituents may be independently selected from the group consisting of a halogen atom (e.g. F, Cl, Br, I), a linear or branched $C_{1-6}$-alkyl group, a linear or branched $C_{1-6}$ alkoxy group, a formyl group, a hydroxy group, a trifluoromethyl group, a trifluoromethoxy group, a $-CO-C_{1-6}$-alkyl group, a cyano group, a nitro group, a carboxy group, a $-CO-O-C_{1-6}$-alkyl group, a $-CO-NR^AR^B$-moiety, a $-CO-NH-NR^CR^D$-moiety, an $-SH$, an $-S-C_{1-6}$-alkyl group, an $-SO-$ $C_{1-6}$-alkyl group, an —$SO_2$—$C_{1-6}$-alkyl group, a —$C_{1-6}$-alkylene-S—$C_{1-6}$-alkyl group, a —$C_{1-6}$-alkylene-SO—$C_{1-6}$-alkyl group, a —$C_{1-6}$-alkylene-$SO_2$—$C_{1-6}$-alkyl group, an —$NH_2$-moiety, an NHR'-moiety or an NR'R''-moiety, wherein R' and R'' independently represent a linear or branched $C_{1-6}$-alkyl group, a $C_{1-6}$-alkyl group substituted by one or more hydroxy groups and a —$C_{1-6}$-alkylene-$N^E R^F$ group, whereby $R^A$, $R^B$, identical or different, represent hydrogen or a $C_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, $C_{1-6}$-alkyl groups and/or which may contain at least one further heteroatom selected from the group consisting of nitrogen, oxygen and sulphur as a ring member, $R^C$, $R^D$, identical or different, represent a hydrogen atom, a $C_{1-6}$-alkyl group, a —CO—O—$C_{1-6}$-alkyl group, a $C_{3-8}$-cycloalkyl group, a $C_{1-6}$-alkylene-$C_{3-8}$-cycloalkyl group, $C_{1-6}$-alkylene-O—$C_{1-6}$-alkyl group or a $C_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of $C_{1-6}$-alkyl group, a —CO—$C_{1-5}$-alkyl group, a —CO—C—$C_{1-6}$-alkyl group, a —CO—NH—$C_{1-6}$-alkyl group, a —CS—NH—$C_{1-6}$-alkyl group, an oxo group, a $C_{1-6}$-alkyl group substituted with one or more hydroxy groups, a $C_{1-6}$-alkylene-O—$C_{1-6}$-alkyl group and a —CO—$NH_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen arid sulphur as a ring member.

Preferred aryl groups, which may optionally be at least mono-substituted, are phenyl and naphthyl.

If one or more of the residues $R^3$—$R^8$ represents or comprises a heteroaryl group, which is substituted by one or more, e.g. 1, 2, 3, 4 or 5 substituents, unless defined otherwise, each of the substituents may be independently selected from the group consisting of a halogen atom (e.g. F, Cl, Br, I), a linear or branched $C_{1-6}$-alkyl group, a linear or branched $C_{1-6}$ alkoxy group, a formyl group, a hydroxy group, a trifluoromethyl group, a trifluoromethoxy group, a —CO—$C_{1-6}$-alkyl group, a cyano group, a carboxy group, a —CO—O—$C_{1-6}$-alkyl group, a —CO—$NR^A R^B$-moiety, a —CO—NH—$NR^C R^D$-moiety, an —S—$C_{1-6}$-alkyl group, an —SO—$C_{1-6}$-alkyl group, an —$SO_2$—$C_{1-6}$-alkyl groups a —$C_{1-6}$-alkylene-S—$C_{1-6}$C-alkyl group, a —$C_{1-6}$-alkylene-SO—$C_{1-6}$-alkyl group, a —$C_{1-6}$-alkylene-$SO_2$-$C_{1-6}$-alkyl group, a $C_{1-6}$-alkyl group substituted by one or more hydroxy groups and a —$C_{1-6}$-alkylene-$NR^E R^F$ group, whereby $R^A$, $R^B$, identical or different, represent hydrogen or a $C_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, $C_{1-6}$ alkyl groups and/or which may contain at least one further heteroatom selected from the group consisting of nitrogen, oxygen and sulphur as a ring member, $R^C$, $R^D$, identical or different, represent a hydrogen atom, a $C_{1-6}$-alkyl group, a —CO—O—$C_{1-6}$-alkyl group, a $C_{3-8}$-cycloalkyl group, a $C_{1-6}$-alkylene-$C_{3-8}$-cycloalkyl group, $C_{1-6}$-alkylene-O—$C_{1-6}$-alkyl group or a $C_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of $C_{1-6}$ alkyl group, a —CO—$C_{1-6}$-alkyl group, a —CO—O—$C_{1-6}$-alkyl group, a —CO—NH—$C_{1-6}$-alkyl group, a —CS—NH—$C_{1-6}$-alkyl group, an oxo group a $C_{1-6}$-alkyl group substituted with one or more hydroxy groups, a $C_{1-6}$-alkylene-O—$C_{1-6}$-alkyl group and a —CO—$NH_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$-alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen and sulphur as a ring member.

The heteroatoms, which are present as ring members in the heteroaryl radical, may, unless defined otherwise, independently be selected from the group consisting of nitrogen, oxygen and sulphur. Preferably a heteroaryl radical may comprise 1, 2 or 3 heteroatoms independently selected from the group consisting of N, O and S as ring members.

Suitable heteroaryl groups, which may optionally be at least mono-substituted, may preferably be selected from the group consisting of thienyl, furyl, pyrrolyl, pyridinyl, imidazolyl, pyrimidinyl, pyrazinyl, indolyl, chinolinyl, isochinolinyl, benzo[1,2,5]-thiodiazolyl, benzo[b]thiophenyl, benzo[b]furanyl, imidazo[2,1-b]thiazolyl, triazolyl, and pyrazolyl, more preferably be selected from the group consisting of thienyl-, benzo[1,2,5]-thiodiazolyl, benzo[b]thiophenyl, imidazo[2,1-b]thiazolyl, triazolyl and pyrazolyl.

If one or more of the residues $R^4$—$R^8$ represents or comprises a linear or branched, saturated or unsaturated aliphatic group such as an alkyl group, which is substituted by one or more, e.g. 1, 2, 3, 4 or 5 substituents, unless defined otherwise, each of the substituents may be independently selected from the group consisting of hydroxy, fluorine, chlorine, bromine, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein the $C_{1-4}$-alkyl may in each case be branched or unbranched, and a phenyl group, more preferably be selected from the group consisting of hydroxy, F, Cl, Br, methoxy, ethoxy, $CF_3$ and a phenyl group.

Preferred linear or branched, saturated or unsaturated aliphatic groups, which may be substituted by one or more substituents, may preferably be selected from the group consisting of methyl, ethyl, n-propyl, isopropyl, n-butyl, isobutyl, sec-butyl, tert-butyl, n-pentyl, n-hexyl, n-heptyl, n-octyl, n-nonyl, n-decyl, vinyl, ethinyl, propenyl, propinyl, butenyl and butinyl.

If any of the residues $R^4$—$R^8$ represents or comprises a linear or branched alkylene group, said alkylene group may preferably be selected from the group consisting of methylene —(CH$_2$)—, ethylene —(CH$_2$—CH$_2$)—, n-propylene —(CH$_2$—CH$_2$—CH$_2$)— or iso-propylene —(C(CH$_3$)$_2$)—.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon or $^{15}$N-enriched nitrogen are within the scope of this invention.

Preferred are substituted pyrazoline compounds of general formula I given above, wherein $R^1$ represents an optionally at least mono-substituted phenyl group, $R^2$ represents an optionally at least mono-substituted phenyl group, $R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or $R^3$ represents an optionally at least mono-substituted aryl or heteroaryl group, which may be condensed with an optionally at least mono-substituted mono- or polycyclic ring system, or $R^3$ represents an —NR$^4$R$^5$-moiety, $R^4$ and $R^5$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —SO$_2$—R$^6$-moiety, or an —NR$^7$R$^8$-moiety, $R^6$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^7$ and $R^8$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of a corresponding N-oxide thereof, or a corresponding salt thereof, or a corresponding solvate thereof, whereby the following provisos (disclaimers) may apply, namely that $R^4$ and $R^5$ do not both represent a hydrogen atom, and/or that if one of the residues $R^4$ and $R^5$ represents a hydrogen atom or a linear or branched, saturated or unsaturated, substituted or unsubstituted aliphatic group, the other one of these residues $R^4$ and $R^5$ does not represent a substituted or unsubstituted pyridyl group, a substituted or unsubstituted pyrimidyl group, a substituted or unsubstituted pyridazyl group, a substituted or unsubstituted pyrazinyl group, a substituted or unsubstituted thienyl group, a substituted or unsubstituted benzyl group, a substituted or unsubstituted phenethyl group, a substituted or unsubstituted phenyl group, a substituted or unsubstituted phenyl group, which is condensed (attached) to at least one, optionally substituted ring or ringsystem, an —NH-phenyl-moiety, wherein the phenyl group may be at least mono-substituted, an unsubstituted or substituted thiazole group, or an unsubstituted or substituted [1,3,4]thiadiazole group.

Preferred are also substituted pyrazoline compounds of general formula I given above, wherein $R^1$ represents a phenyl group, which is optionally substituted by one or more substituents independently selected from the group consisting of a linear or branched C$_{1-6}$-alkyl group, a linear or branched C$_{1-6}$-alkoxy group, a halogen atom, CH$_2$F, CHF$_2$, CF$_3$, CN, OH, NO$_2$, —(C=O)—R', SH, SR', SOR', SO$_2$R', NH$_2$, NHR', NR'R", —(C=O)—NH$_2$, —(C=O)—NHR' and —(C=O)—NR'RR", whereby R' and R" for each substituent independently represent linear or branched C$_{1-6}$ alkyl, preferably $R^1$ represents a phenyl group, which is optionally substituted by one or more substituents selected from the group consisting of methyl, ethyl, F, Cl, Br and CF$_3$, more preferably $R^1$ represents a phenyl group, which is substituted with a chlorine atom in the 4-position, and $R^2$—$R^8$ have the meaning given above, optionally in form of a corresponding N-oxide thereof, or a corresponding salt thereof, or a corresponding solvate thereof.

Also preferred are substituted pyrazoline compounds of general formula I given above, wherein $R^2$ represents a phenyl group, which is optionally substituted by one or more substituents independently selected from the group consisting of a linear or branched C$_{1-6}$-alkyl group, a linear or branched C$_{1-6}$-alkoxy group, a halogen atom, CH$_2$F, CHF$_2$, CF$_3$, ON, OH, NO$_2$, —(C=O)—R', SH, SR', SOR', SO$_2$R', NH$_2$, NHR', NR'R", —(C=O)—NH$_2$, —(C=O)—NHR' and —(C=O)—NR'R" whereby R' and R" for each substituent independently represent linear or branched C$_{1-6}$ alkyl, preferably $R^2$ represents a phenyl group, which is optionally substituted by one or more substituents selected from the group consisting of methyl, ethyl, F, Cl, Br and CF$_3$, more preferably $R^2$ a phenyl group, which is di-substituted with two chlorine atoms in the 2- and 4-position, and $R^1$ and $R^3$—$R^3$ have the meaning given above, optionally in form of a corresponding N-oxide thereof, or a corresponding salt thereof, or a corresponding solvate thereof.

Preference is also given to substituted pyrazoline compounds of general formula I given above, wherein $R^3$ represents a saturated or unsaturated, optionally at least mono-substituted, optionally at least one heteroatom as ring member containing C$_{3-8}$ cycloaliphatic group, which may be condensed with an optionally at least mono-substituted mono- or polycyclic ring system, or $R^3$ represents an optionally at least mono-substituted, 5- or 6-membered aryl or heteroaryl group, which may be condensed with an optionally at least mono-substituted mono- or polycyclic ring system, or $R^3$ represents an —NR$^4$R$^5$-moiety, preferably $R^3$ represents a saturated, optionally at least mono-substituted, optionally one or more nitrogen-atoms as ring member containing C$_{3-8}$ cycloaliphatic group, which may be condensed with an optionally at least mono-substituted mono- or polycyclic ring system, or R³ represents an —NR⁴R⁵-moiety, more preferably R³ represents a pyrrolidinyl group, a piperidinyl group or a piperazinyl group, whereby each of these groups may be substituted with one or more $C_{1-6}$-alkyl groups, or R³ represents an —NR⁴R⁵-moiety and R¹, R² and R⁴—R⁸ have the meaning given above, optionally in form of a corresponding N-oxide thereof, or a corresponding salt thereof, or a corresponding solvate thereof.

Furthermore, substituted pyrazoline compounds of general formula I given above are preferred, wherein R⁴ and R⁵, identical or different, represent a hydrogen atom, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system and/or bonded via a methylene (—CH₂—) or ethylene (—CH₂—CH₂)-group, an —SO₂—R⁶-moiety, or an —NR⁷R⁸-moiety, preferably one of these residues R⁴ and R⁵ represents a hydrogen atom and the other one of these residues R⁴ and R⁵ represents a saturated or unsaturated, optionally at least mono-substituted, optionally at least one heteroatom as ring member containing $C_{3-8}$-cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system, an —SO₂—R⁶-moiety or an —NR⁷R⁸-moiety, or R⁴ and R⁵, identical or different, each represent a $C_{1-6}$ alkyl group, more preferably one of these residues R⁴ and R⁵ represents a hydrogen atom and the other one of these residues R⁴ and R⁵ represents an optionally at least mono-substituted pyrrolidinyl group, an optionally at least mono-substituted piperidinyl group, an optionally at least mono-substituted piperazinyl group, an optionally at least mono-substituted triazolyl group, an —SO—R⁶-moiety, or an —NR⁷R⁸-moiety, or R⁴ and R⁵, identical or different, represent a methyl group, an ethyl group, an n-propyl group, an isopropyl group, an n-butyl group, a sec-butyl group or a tert.-butyl group, and R¹—R³ and R⁶—R⁸ have the meaning given above, optionally in form of a corresponding N-oxide thereof, or a corresponding salt thereof, or a corresponding solvate thereof.

Also preferred are substituted pyrazoline compounds of general formula I given above, wherein R⁶ represents a linear or branched, saturated or unsaturated, optionally at least mono-substituted $C_{1-6}$ aliphatic group, a saturated or unsaturated, optionally at least mono-substituted, optionally at least one heteroatom as ring member containing $C_{3-8}$ cycloaliphatic group, which may be condensed with a mono- or polycyclic ring-system, or an optionally at least mono-substituted, 5- or 6-membered aryl or heteroaryl group, which may be condensed with a mono- or polycyclic ring system and/or bonded via a methylene (—CH₂—) or ethylene (—CH₂—CH₂)-group, preferably R⁶ represents a $C_{1-6}$-alkyl group, a saturated, optionally at least mono-substituted cycloaliphatic group, which may be condensed with a mono- or polycyclic ring-system, or a phenyl group, which is optionally substituted with one or more $C_{1-6}$ alkyl groups, and R¹—R⁵, R⁷ and R⁸ have the meaning given above, optionally in form of a corresponding N-oxide thereof, or a corresponding salt thereof, or a corresponding solvate thereof.

Moreover substituted pyrazoline compounds of general formula I given above are preferred, wherein R⁷ and R⁸, identical or different, represent a hydrogen atom, an unbranched or branched, saturated or unsaturated, optionally at least mono-substituted $C_{1-6}$ aliphatic radical, a saturated or unsaturated, optionally at least mono-substituted, optionally at least one heteroatom as ring member containing $C_{3-8}$ cycloaliphatic group, which may be condensed with an optionally at least mono-substituted mono- or polycyclic ring system, or an optionally at least mono-substituted, 5- or 6 membered aryl or heteroaryl group, which may be condensed with an optionally at least mono-substituted mono- or polycyclic ring system and/or bonded via a methylene (—CH₂—) or ethylene (—CH₂—CH₂)-group, preferably represent a hydrogen atom or a $C_{1-6}$ alkyl radical, and R¹—R⁶ have the meaning given above, optionally in form of a corresponding N-oxide thereof, or a corresponding salt thereof, or a corresponding solvate thereof.

Particularly preferred are substituted pyrazoline compounds of general formula I

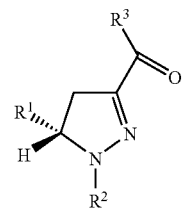

wherein

R¹ represents a phenyl group, which is optionally substituted by one or more substituents independently selected from the group consisting of methyl, ethyl, F, Cl, Br and CF₃, R² represents a phenyl group, which is optionally substituted by one or more substituents independently selected from the group consisting of methyl, ethyl, F, Cl, Br and CF₃.

R³ represents a pyrrolidinyl group, a piperdinyl group or a piperazinyl group, whereby each of these groups may be substituted with one or more $C_{1-6}$-alkyl groups, or R³ represents an —NR⁴R⁵-moiety, one of the residues R⁴ and R⁵ represents a hydrogen atom and the other one of these residues R⁴ and R⁵ represents an optionally at least mono-substituted pyrrolidinyl group; an optionally at least mono-substituted piperidinyl group; an optionally at least mono-substituted piperazinyl group; an optionally at least mono-substituted triazolyl group; an —SO₂—R⁶-moiety; or an —NR⁷R⁸-moiety, or R⁴ and R⁵, identical or different, represent a methyl group, an ethyl group, an n-propyl group, an isopropyl group, an n-butyl group, a sec-butyl group or a tert.-butyl group, R⁶ represents a $C_{1-6}$-alkyl group; a saturated, optionally at least mono-substituted cycloaliphatic group, which may be condensed with a mono- or polycyclic ring-system; or a phenyl group, which is optionally substituted with one or more $C_{1-6}$ alkyl groups, and R⁷ and R⁸, identical or different, represent a hydrogen atom or a $C_{1-6}$ alkyl radical optionally in form of a corresponding N-oxide thereof, or a corresponding salt thereof, or a corresponding solvate thereof.

Also particularly preferred are substituted pyrazoline compounds of general formula I

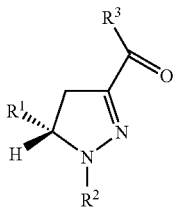

wherein
- $R^1$ represents a phenyl group, which is optionally substituted with 1, 2, 3, 4 or 5 substituents independently selected from the group consisting of linear or branched $C_{1-6}$-alkyl, linear or branched $C_{1-6}$-alkoxy, F, Cl, Br, I, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R", whereby R' and R" at each occurrence independently represent a linear or branched $C_{1-6}$ alkyl group,
- $R^2$ represents a phenyl group, which is optionally substituted with 1, 2, 3, 4 or 5 substituents independently selected from the group consisting of linear or branched $C_{1-6}$-alkyl, linear or branched $C_{1-6}$-alkoxy, F, Cl, Br, I, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R", whereby R' and R" at each occurrence independently represent a linear or branched $C_{1-6}$ alkyl group,
- $R^3$ represents a saturated or unsaturated $C_{3-8}$ cycloaliphatic group, whereby said $C_{3-8}$ cycloaliphatic group is optionally substituted with 1, 2, 3 or 4 substituents independently selected from the group consisting of linear or branched $C_{1-6}$ alkyl, linear or branched $C_{1-6}$ alkoxy, OH, F, Cl, Br, I, CN, $CH_2F$, $CHF_2$, $CF_3$ and oxo (=O) and whereby said $C_{3-8}$ cycloaliphatic group may contain 1, 2 or 3 heteroatoms independently selected from the group consisting of N, O and S as ring members, or
- $R^3$ represents an —$NR^4R^5$-moiety,
- $R^4$ represents a hydrogen atom or a linear or branched $C_{1-6}$-alkyl group,
- $R^5$ represents a linear or branched $C_{1-6}$ alkyl group; an —$SO_2$—$R^6$-moiety; a saturated or unsaturated $C_{3-8}$ cycloaliphatic group, whereby said $C_{3-8}$ cycloaliphatic group is optionally substituted with 1, 2, 3 or 4 substituents independently selected from the group consisting of linear or branched $C_{1-6}$ alkyl group, a linear or branched $C_{1-6}$ alkoxy group, OH, F, Cl, Br, I, ON $CH_2F$, $CHF_2$, $CF_3$ and oxo (=O) and whereby said $C_{3-8}$ cycloaliphatic group may contain 1, 2 or 3 heteroatoms independently selected from the group consisting of N, O and S as ring members, and
- $R^5$ represents a phenyl group, which is optionally substituted with 1, 2, 3, 4 or 5 substituents independently selected from the group consisting of a linear or branched $C_{1-6}$-alkyl group, a linear or branched $C_{1-6}$-alkoxy group, F, Cl, Br, I, CHF, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R", whereby R' and R" at each occurrence independently represent a linear or branched $C_{1-6}$ alkyl group, optionally in form of a corresponding N-oxide thereof, or a corresponding salt thereof, or a corresponding solvate thereof.

Also particularly preferred are substituted pyrazoline compounds of general formula I

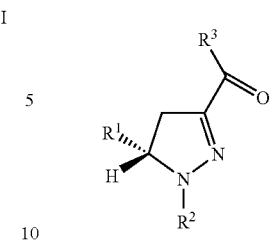

wherein
- $R^1$ represents a phenyl group, which is optionally substituted with 1, 2, 3, 4 or 5 substituents independently selected from the group consisting of methyl, ethyl, F, Cl, Br and $CF_3$,
- $R^2$ represents a phenyl group, which is optionally substituted with 1, 2, 3, 4 or 5 substituents independently selected from the group consisting of methyl, ethyl, F, Cl, Br and $CF_3$,
- $R^3$ represents a pyrrolidinyl group, a piperidinyl group or a piperazinyl group, whereby each of these groups may be substituted with one or more of $C_{1-6}$-alkyl groups, or $R^3$ represents an —$NR^4R^5$-moiety,
- $R^4$ represents a hydrogen atom or a linear or branched $C_{1-6}$-alkyl group,
- $R^5$ represents a linear or branched $C_{1-6}$ alkyl group; an —$SO_2$—$R^6$-moiety; a pyrrolidinyl group; a piperidinyl group; a piperazinyl group; a homo-piperazinyl group; a morpholinyl group; a triazolyl group; whereby each of the heterocyclic rings may be substituted with one or more, identical or different, $C_{1-6}$-alkyl groups, and
- $R^6$ represents a phenyl group, which is optionally substituted with one or more $C_{1-6}$ alkyl groups, which may be identical or different, optionally in form of a corresponding N-oxide thereof, or a corresponding salt thereof, or a corresponding solvate thereof.

Also particularly preferred are substituted pyrazoline compounds of general formula I

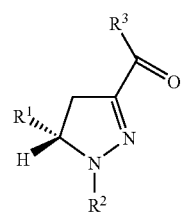

wherein
- $R^1$ represents a phenyl ring, which is mono-substituted with a halogen atom, preferably a chlorine atom, in its 4-position,
- $R^2$ represents a phenyl ring, which is di-substituted with two halogen atoms, preferably chlorine atoms, in its 2- and 4-position,
- $R^3$ represents a pyrrolidinyl group, a piperidinyl group, a piperazinyl group, a homo-piperazinyl group, a morpholinyl group, or an —$NR^4R^5$-moiety,
- $R^4$ represents a hydrogen atom or a linear or branched $C_{1-6}$-alkyl group,
- $R^5$ represents a linear or branched $C_{1-6}$ alkyl group; an —$SO_2$—$R^6$-moiety; a pyrrolidinyl group; a piperidinyl group; a piperazinyl group; a homo-piperazinyl group: a morpholinyl group; or a triazolyl group whereby each of the heterocyclic rings may be substituted with one or more, identical or different, $C_{1-6}$-alkyl groups, and $R^6$ represents a phenyl group, which is optionally substituted with one or more $C_{1-6}$ alkyl groups, which may be identical or different, optionally in form of a corresponding N-oxide thereof, or a corresponding salt thereof, or a corresponding solvate thereof.

Most particularly preferred is the compound (S)-N-piperidinyl-5-(4-chloro-phenyl)-1-(2,4-dichlorophenyl)-4,5-dihydro-1H-pyrazol-3-carboxamide:

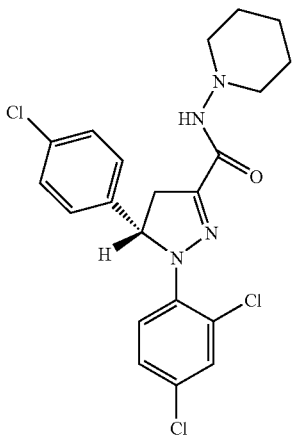

optionally in the form of a corresponding N-oxide, a corresponding salt or a corresponding solvate.

In another aspect the present invention also provides a process for the preparation of substituted pyrazoline compounds of general formula I given above, according to which at least one compound of general formula IIa

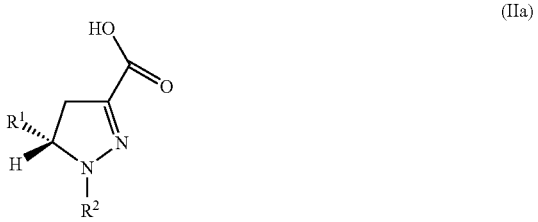

(IIa)

wherein $R^1$ and $R^2$ have the meaning given above, is optionally transferred under inert atmosphere to a compound of general formula (III) via reaction with an activating agent

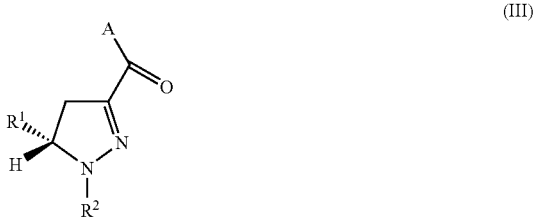

(III)

wherein the substituents $R^1$ and $R^2$ have the meaning given above and A represents a leaving group, preferably a chlorine atom, said compound being optionally isolated and/or optionally purified, and at least one compound of general formula (IIa) is reacted with a compound of general formula $R^3H$, wherein $R^3$ represents an —$NR^4R^5$-moiety, with $R^4$ and $R^5$ having the meaning given above, under inert atmosphere to yield a substituted pyrazoline compound of general formula I, wherein $R^3$ represents an —$NR^4R^5$-moiety, or at least one compound of general formula (III) is reacted with a compound of the general formula $R^3H$, in which $R^3$ has the meaning given above under inert atmosphere to yield a compound of general formula (I), which is optionally isolated and/or optionally purified.

Preferably the compound IIa is obtained from a mixture comprising the enantiomers

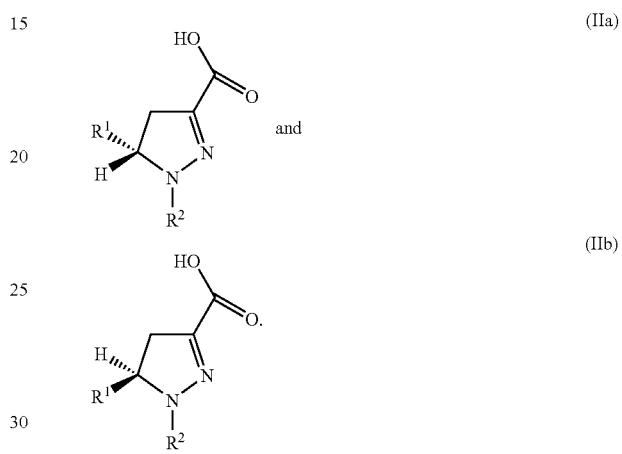

The compound (IIa) may be obtained from the mixture of the enantiomers by means well known to those skilled in the art. Preferably, the compound IIa is obtained from the mixture in form of an addition compound with a chiral base, preferably Brucine, Quinine or (–)-Cinchonidine, and preferably liberated from the addition compound.

Preferably the mixture comprising the enantiomers IIa and IIb may be obtained by reacting at least one benzaldehyde compound of general formula (IV)

(IV)

wherein $R^1$ has the meaning given above, is reacted with a pyruvate compound of general formula (V)

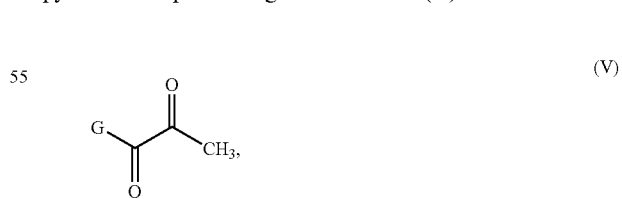

(V)

wherein G represents an OR group with R being a branched or unbranched $C_{1-6}$ alkyl radical, preferably an ethyl radical, or G represents an O⁻K group with K being a cation, preferably a monovalent cation, more preferably an alkali metal cation, even more preferably a sodium cation, to yield a compound of general formula (VI)

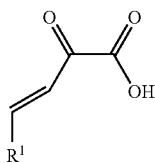
(VI)

wherein R¹ has the meaning given above, which is optionally isolated and/or optionally purified, and which is reacted with an optionally substituted phenyl hydrazine of general formula (VII)

(VII)

or a corresponding salt thereof, wherein R² has the meaning given above, under inert atmosphere, to yield a mixture of compounds

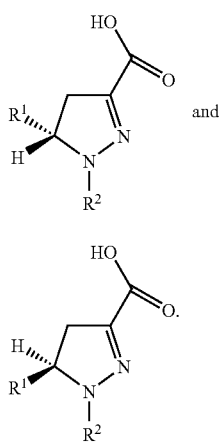
(IIa) and (IIb)

The inventive process is also illustrated in scheme I given below:

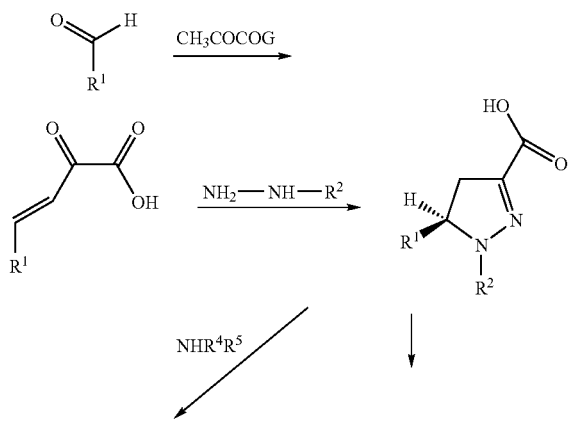

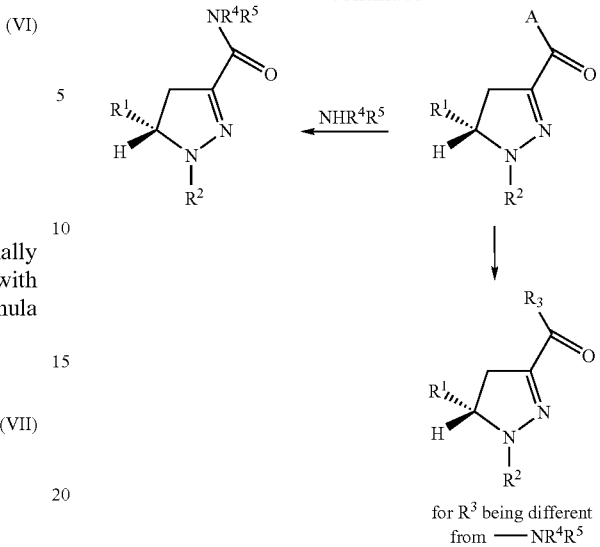

for R³ being different from —NR⁴R⁵

The reaction of the benzaldehyde compound of general formula IV with a pyruvate compound of general formula V is preferably carried out in the presence of at least one base, more preferably in the presence of an alkali metal hydroxide such as sodium hydroxide or potassium hydroxide or an alkali metal methoxide such as sodium methoxide, as described, for example, in Synthetic communications, 26(11), 2229-33, (1996). The respective description is hereby incorporated by reference and forms part of the disclosure. Preferably sodium pyruvate may be used as the pyruvate compound. Preferably said reaction is carried out in a protic reaction medium such as a $C_{1-4}$ alkyl alcohol or mixtures of these. Mixtures of such alcohols with water, E.G. ethanol/water may also be used.

Reaction temperature as well as the duration of the reaction may vary over a broad range. Preferred reaction temperatures range from −10° C. to the boiling point of the reaction medium. Suitable reaction times may vary for example from several minutes to several hours.

Also preferred the reaction of the benzaldehyde compound of general formula IV with a pyruvate compound of general formula V is carried out under acid catalysed conditions, more preferably by refluxing the mixture in dichloromethane in the presence of copper(II)trifluoromethanesulfonate as described, for example, in Synlett, (1), 147-149, 2001. The respective description is hereby incorporated by reference and forms part of the disclosure.

The reaction of the compound of general formula (VI) with an optionally substituted phenyl hydrazine of general formula (VII) is preferably carried out in a suitable reaction medium such as $C_{1-4}$-alcohols or ethers such as dioxane or Tetrahydrofuran or mixtures of at least two of these afore mentioned compounds. Also preferably, said reaction may be carried out in the presence of an acid, whereby the acid may be organic such as acetic acid and/or inorganic such as hydrochloric acid. Furthermore, the reaction may also be carried out in the presence of a base such as piperidine, piperazine, sodium hydroxide, potassium hydroxide, sodium methoxide or sodium ethoxide, or a mixture of at least two of these bases may also be used.

Reaction temperature as well as the duration of the reaction may vary over a broad range. Suitable reaction temperatures range from room temperature, i.e, approximately 25° C. to the boiling point of the reaction medium. Suitable reaction times may vary for example from several minutes to several hours.

The carboxylic group of the compound of general formula (III) may be activated for further reactions by the introduction of a suitable leaving group according to conventional methods well known to those skilled in the art. Preferably the compounds of general formula (VI) are transferred into an acid chloride, an acid anhydride, a mixed anhydride, a $C_{1-4}$ alkyl ester, an activated ester such as p-nitrophenylester. Other well known methods for the activation of acids include the activation with N,N-dicyclohexylcarbodiimide or benzotriazol-N-oxotris (dimethylamino)phosphonium hexafluorophosphate (BOP)).

If said activated compound of general formula (III) is an acid chloride, it is preferably prepared by reaction of the corresponding acid of general formula (IIa) with thionyl chloride or oxalyl chloride, whereby said chlorinating agent is also used as the solvent, Also preferably an additional solvent may be used. Suitable solvents include hydrocarbons such as benzene, toluene or xylene, halogenated hydrocarbons such as dichloromethane, chloroform or carbon tetrachloride, ethers such as diethyl ether, dioxane, Tetrahydrofuran or dimethoxyethane. Mixtures of two or more solvents from one class or two or more solvents from different classes may also be used. Preferred reaction temperature range from 0° C. to the boiling point of the solvent and reaction times from several minutes to several hours.

If said activated compound of general formula (III) is a mixed anhydride, said anhydride may preferably be prepared, for example, by reaction of the corresponding acid of general formula (IIa) with ethyl chloroformate in the presence of a base such as triethylamine or pyridine, in a suitable solvent.

The reaction of general formula (IIa) with a compound of general formula $HR^3$ to yield compounds of general formula I, wherein $R^3$ represents an —$NR^4R^5$ moiety is preferably carried out in presence of a base such as triethylamine in a reaction medium such as methylenechloride. The temperature is preferably in the range from 0° C. to the boiling point of the reaction medium. The reaction time may vary over a broad range, e.g. from several hours to several days.

The reaction of general formula (IIa) with a compound of general formula $HR^3$ to yield compounds of general formula I, wherein $R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system may be carried out according to conventional methods well known to those skilled in the art, e.g. from Pascual, A., J. Prakt. Chem., 1999, 341(7), 695-700; Lin, S. et al., Heterocycles, 2001, 55(2), 265-277; Rao, P. et al., J. Org. Chem., 2000, 65(22), 7323-7344, Pearson D. E and Buehler, C. A., Synthesis, 1972, 533-542 and references cited therein. The respective descriptions are hereby incorporated by reference and form part of the present disclosure.

Preferably said reaction is carried out in the presence of a Lewis acid, which is preferably selected from the group consisting of $FeCl_3$, $ZnCl_2$, and $AlCl_3$, in a suitable reaction medium such as toluene, benzene, Tetrahydrofuran or similar. The temperature is preferably in the range from 0° C. to the boiling point of the reaction medium, more preferably from 15 to 25° C. The reaction time may vary over a broad range, e.g. from several minutes to several hours.

The afore mentioned reactions involving the synthesis of the 4,5-dihydro-pyrazole ring or the reaction of a compound comprising said ring are carried out under an inert atmosphere, preferably nitrogen or argon, to avoid oxidation of the ring-system.

During the processes described above the protection of sensitive groups or of reagents may be necessary and/or desirable. The introduction of conventional protective groups as well as their removal may be performed by methods well-known to those skilled in the art.

In a further aspect the present invention also provides a process for the preparation of salts of substituted pyrazoline compounds of general formula (I), wherein at least one compound of general formula (I) having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted pyrazoline compounds of general formula (I), wherein at least one compound of general formula (I) having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions. Especially this covers any physiologically acceptable salt.

Solvates, preferably hydrates, of the substituted pyrazoline compounds of general formula (I), of corresponding N-oxides or of corresponding salts thereof may also be obtained by standard procedures known to those skilled in the art.

Substituted pyrazoline compounds of general formula I, which comprise nitrogen-atom containing saturated, unsaturated or aromatic rings may also be obtained in the form of their N-oxides by methods well known to those skilled in the art.

Those skilled in the art understand that the term substituted pyrazoline compounds as used herein is to be understood as encompassing derivatives such as others, esters and complexes of these compounds as well, The term "derivatives" as used in this application is defined here as meaning a chemical compound having undergone a chemical derivation starting from an acting (active) compound to change (ameliorate for pharmaceutical use) any of its physico-chemical properties, especially a so-called prodrug, e.g. their esters and ethers. Examples of well known methods of producing a prodrug of a given acting compound are known to those skilled in the art and can be found e.g. in Krogsgaard-Larsen et al., Textbook of Drugdesign and Discovery, Taylor & Francis (April 2002). The respective description is hereby incorporated by reference and forms part of the disclosure.

Those skilled in the art understand that substituents of the inventive compounds, particularly substituent $R^3$, may lead to stereoisomers, which are also covered by the present invention.

The purification and isolation of the inventive substituted pyrazoline compounds of general formula (I) and its intermediates, or a salt thereof, or an N-oxide thereof, or a solvate or any intermediate thereof may, if required, be carried out by conventional methods known to those skilled in the art, e.g. chromatographic methods or recrystallization.

The substituted pyrazoline compounds of general formula (I) given below, corresponding N-oxides, corresponding salts thereof and corresponding solvates are toxicologically acceptable and are therefore suitable as pharmaceutical active substances for the preparation of medicaments.

It has been found that the substituted pyrazoline compounds of general formula I given below, N-oxides thereof, corresponding salts and corresponding solvates have a high affinity to cannabinoid receptors, particularly cannabinoid 1 ($CB_1$)-receptors, i.e. they are selective ligands for the ($CB_1$)-receptor and act as modulators, e.g. antagonists, inverse agonists or agonists, on these receptors. In particular, these pyrazoline compounds show little or no development of tolerance during treatment, particularly with respect to food intake, i.e. if the treatment is interrupted for a given period of time and then continued afterwards, the inventively used pyrazoline compounds will again show the desired effect. After ending the treatment with the pyrazoline compounds, the positive influence on the body weight is found to continue.

Furthermore, these pyrazoline compounds show relatively weak Herg channel affinity, thus a low risk of prolongation of the QT-interval is to be expected for these compounds.

In summary, the inventively used pyrazoline compounds are distinguished by a broad spectrum of beneficial effects, while at the same time showing relatively little undesired effects, i.e. effects which do not positively contribute to or even interfere with the well being of the patient.

The chronic administration of the CB1 antagonist (S)-N-piperidinyl-5-(4-chlorophenyl)-1-(2,4-dichlorophenyl)-4,5-dihydro-1H-pyrazole-3-carboxamide significantly decreased body weight in animals made obese by exposure to a simplified cafeteria diet containing high-fat diet, chocolate and ground peanuts to mirror a typical Western diet. After 28 days of drug treatment, the body weight of rats given (S)-N-piperidinyl-5-(4-chlorophenyl )-1-(2,4-dichlorophenyl)-4,5-dihydro-1H-pyrazole-3-carboxamide was lower than those of the vehicle-treated controls.

Moreover, the compound (S)-N-piperidinyl-5-(4-chlorophenyl)-1-(2,4-dichlorophenyl)-4,5-dihydro-1H-pyrazole-3-carboxamide—in particular following chronic administration—has a positive effect on plasma lipids, for instance triacylglycerol and glycerol, that seems to be independent of that produced by the weight loss.

Thus, an other aspect of the present invention relates to a medicament comprising at least one substituted pyrazoline compound of general formula I, optionally in form of a corresponding N-oxide thereof, or a corresponding salt thereof, or a corresponding solvate thereof, and optionally one or more pharmaceutically acceptable excipients. It is preferred that the inventive compounds are present in the medicament with an enantiomeric excess with respect to their other enantiomer (resulting from the stereocenter at the 5-position) of at least 90%, more preferably at least 95%, yet more preferably of at least 99%. Most preferably, the inventive medicament comprises the substituted pyrazoline compound of general formula I in pure form, i.e. essentially free from its other enantiomer.

The inventive medicament may preferably also comprise any of the inventive pyrazoline compounds or combinations of at least two of these pyrazoline compounds given above.

Said medicament may also comprise any combination of one or more of the substituted pyrazoline compounds of general formula I given above, corresponding N-oxides thereof, physiologically acceptable salts thereof or physiologically acceptable solvates thereof.

Preferably said medicament is suitable for the modulation (regulation) of cannabinoid-receptors, preferably cannabinoid 1 ($CB_1$) receptors for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferably said medicament is suitable for the prophylaxis and/or treatment of psychosis.

Also particularly preferably said medicament is suitable for the prophylaxis and/or treatment of food intake disorders, preferably bulimia, anorexia, cachexia, obesity and/or type II diabetus mellitus (non-insuline dependent diabetes mellitus), more preferably obesity. The inventive medicament also seems to be active in the prophylaxis and/or treatment of appetency disorders, e.g, the pyrazoline compounds of general formula I also reduce the desire for sweets.

Also particularly preferably said medicament is suitable for the prophylaxis and/or treatment of cancer, preferably for the prophylaxis and/or treatment of one or more types of cancer selected from the group consisting of brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Particularly preferably said medicament is suitable for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Thus, the inventive medicament is active in the treatment of abstinence, craving reduction and relapse prevention of alcohol intake. The inventive medicament can also be used in the prophylaxis and/or treatment of smoking addiction, cessation and/or dependence including treatment for craving reduction and relapse prevention of tobacco smoking.

Medicaments and/or drugs, which are frequently the subject of misuse include opioids, barbiturates, cannabis, cocaine, amphetamines, phencyclidine, hallucinogens and benzodiazepines.

The medicament is also suitable for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone; schizophrenia, anxiety, depression, epilepsy, neurodegenerative disorders, cerebellar disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and nonnarcotic analgesics, or for influencing intestinal transit.

The medicament is also suitable for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression; behavioural addictions; attention deficit disorders; Tourette's syndrome; suppression of reward-related behaviours; e g. conditioned place avoidance such as suppression of cocaine- and morphine induced conditioned place preference, impulsivity; sexual dysfunction; preferably for the prophylaxis and/or treatment of one or more types of sexual dysfunction selected from the group consisting of erectile difficulty and female sexual dysfunction; seizure disorders; nausea; emesis; neuroinflammatory disease, preferably for the prophylaxis and/or treatment of one or more types of neuroinflammatory diseases selected from the group consisting of multiple sclerosis, demyolinisation related disorders, Guillan-Barré syndrome, viral encephalitis and cerebrovascular accidents: neurological disorders; muscle spasticity, traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal isohemima, myocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis; cerebral apoplexy; craniocerebral trauma; neuropathic pain disorders; gastric ulcers atherosclerosis and liver cirrhosis.

Another aspect of the present invention is the use of at least one substituted pyrazoline compound of general formula I given above as suitable active substances, optionally in form of a corresponding N-oxide thereof, or a corresponding salt thereof, or a corresponding solvate thereof, and optionally one or more pharmaceutically acceptable excipients, for the preparation of a medicament for the modulation of cannabinoid-receptors, preferably cannabinoid 1 ($CS_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferred is the use of at least one of the respective pyrazoline compounds, optionally in form of a corresponding N-oxide thereof, or a corresponding salt thereof, or a corresponding solvate thereof, and optionally one or more pharmaceutically acceptable excipients, for the preparation of a medicament for the prophylaxis and/or treatment of psychosis.

Also particularly preferred is the use of at least one of the respective pyrazoline compounds, optionally in form of a corresponding N-oxide thereof, or a corresponding salt thereof, or a corresponding solvate thereof, and optionally one or more pharmaceutically acceptable excipients, for the preparation of a medicament for the prophylaxis and/or treatment of food intake disorders, preferably bulimia, anorexia, cachexia, obesity and/or type II diabetus mellitus (non-insuline dependent diabetes mellitus), more preferably obesity.

Also particularly preferred is the use of at least one of the respective pyrazoline compounds, optionally in form of a corresponding N-oxide thereof, or a corresponding salt thereof, or a corresponding solvate thereof, and optionally one or more pharmaceutically acceptable excipients, for the preparation of a medicament for the prophylaxis and/or treatment of cancer, preferably for the prophylaxis and/or treatment of one or more types of cancer selected from the group consisting of brain cancer, bone cancer, tip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, more preferably for the prophylaxis and/or treatment of one or more types of cancer selected from the group consisting of colon cancer, bowel cancer and prostate cancer.

Also particularly preferred is the use of at least one of the respective pyrazoline compounds, optionally in form of a corresponding N-oxide thereof, or a corresponding salt thereof, or a corresponding solvate thereof, and optionally one or more pharmaceutically acceptable excipients, for the preparation of a medicament for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction and/or nicotine abuse and/or nicotine addiction.

Medicaments/drugs, which are frequently the subject of misuse include opioids, barbiturates, cannabis, cocaine, amphetamines, phencyclidine, hallucinogens and benzodiazepines.

Also preferred is the use of at least one of the respective pyrazoline compounds, optionally in form of a corresponding N-oxide thereof, or a corresponding salt thereof, or a corresponding solvate thereof and optionally one or more pharmaceutically acceptable excipients, for the preparation of a medicament for the prophylaxis and/or treatment of one or more disorders selected from the group consisting of bone disorders, preferably osteoporosis (e.g. osteoporosis associated with a genetic predisposition, sex hormone deficiency, or ageing), cancer-associated bone disease or Paget's disease of bone, schizophrenia, anxiety, depression, epilepsy, neurodegenerative disorders, cerebellar disorders, spinocerebellar disorders, cognitive disorders, cranial trauma, head trauma, stroke, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, medicament-induced movement disorders, dystonia, endotoxemic shock, hemorrhagic shock, hypotension, insomnia, immunologic disorders, sclerotic plaques, vomiting, diarrhoea, asthma, memory disorders, pruritus, pain, or for potentiation of the analgesic effect of narcotic and non-narcotic analgesics, or for influencing intestinal transit.

Also particularly preferred is the use of at least one of the of pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding solvate thereof, and optionally one or more pharmaceutically acceptable excipients, for the preparation of a medicament for the prophylaxis and/or treatment of one or more disorders selected from the group consisting of dementia and related disorders, preferably for the prophylaxis and/or treatment of one or more types of dementia selected from the group consisting of memory loss, vascular dementia, mild cognitive impairment, frontotemporal dementia and Pick's disease; binge eating disorders; juvenile obesity; drug induced obesity; atypical depression, behavioural addictions; attention deficit disorders; Tourette's syndrome; suppression of reward-related behaviours; e.g. conditioned place avoidance such as suppression of cocaine- and morphine induced conditioned place preference; impulsivity, sexual dysfunction; preferably for the prophylaxis and/or treatment of one or more types of sexual dysfunction selected from the group consisting of erectile difficulty and female sexual dysfunction;

seizure disorders; nausea; emesis; neuroinflammatory disease, preferably for the prophylaxis and/or treatment of one or more types of neuroinflammatory diseases selected from the group consisting of multiple sclerosis, demyelinisation related disorders, Guillan-Barré syndrome, viral encephalitis and cerebrovascular accidents; neurological disorders; muscle spasticity; traumatic brain injury; spinal cord injury; inflammation and immunomodulatory disorders, preferably for the treatment and/or prophylaxis of one or more types of inflammation and immunomodulatory disorders selected from the group consisting of cutaneous T-cell lymphoma, rheumatoid arthritis, systemic lupus erythematosus, sepsis, sarcoidosis, idiopathic pulmonary fibrosis, bronchopulmonary dysplasia, retinal disease, scleroderma, renal ischemia, mycocardial infarction, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, chronic obstructive pulmonary disease and bronchitis: cerebral apoplexy; craniocerebral trauma; neuropathic pain disorders; gastric ulcers; atheriosclerosis and liver cirrhosis.

Dementia is a disease characterized by the progressive deterioration in cognitive and social adaptive functions that can eventually interfere with the patient's ability to live independently. Dementia also constitutes of impairment in short- and long-term memory plus additional symptoms, such as problems with abstract thinking, judgment, or personality. An estimated 18 million patients suffer from dementia worldwide. The most common forms of dementia include Alzheimer's disease and vascular dementia. Other forms are frontotemporal dementia and Pick's disease.

Dementia can also be of vascular origin. Vascular dementia (atherosclerotic cerebrovascular disease) is considered to be the second most common dementia of late life, affecting approximately 10-15% of all cases. AD and vascular dementia can exist in isolation or together (mixed dementia). In vascular dementia, atherosclerotic changes in cerebral vessels can lead to reduced local blood flow that results in multiple small strokes (multi-infarct dementia). Vascular dementia is pharmacologically treated by stroke prophylaxis, and by treatment of the cognitive deficit.

Alzheimer's disease (AD), the most common and important form of dementia, is a neurodegenerative disorder that is characterized by progressive impairment of cognitive functions, such as abstract reasoning and memory. Currently, an estimated 2 million people in the United States and 12 million worldwide are afflicted by this disease. Due to increasing life expectancy, it is predicted that there will be over 100 million AD patients worldwide by the year 2050. AD is one of the most prevalent illnesses in the elderly. The majority of AD patients are in their sixties or older. More than 5% of all persons over the age of 70 have significant memory loss due to AD.

AD is mainly characterized through a gradual development of forgetfulness. In further advanced disease stages, other failures in cerebral function become increasingly apparent. This includes impairment of speech, writing, and arithmetic skills.

Visiospacial orientation, such as parking the car, dressing property and giving and understanding directions to a location can become defective or impaired. In late stage disease, patients forget how to use common objects and tools while retaining necessary motor power and co-ordination for these activities.

Schizophrenia is characterized by profound disruption in cognition and emotion, affecting the most fundamental human attributes: language, thought, perception, affect, and sense of self. Positive symptoms include psychotic manifestations, such as hearing internal voices or experiencing other sensations not connected to an obvious source (hallucinations) and assigning unusual significance or meaning to normal events or holding fixed false personal beliefs (delusions). Negative symptoms are characterized by affective flattening and lack of initiative or goals (avolition), loss of usual interests or pleasures (anhedonia), disturbances of sleep and eating, dysphoric mood (depressed, anxious, irritable, or angry mood) and difficulty concentrating or focusing attention.

Major depression is a multifaceted disorder characterized by primarily by dysphoric mood and loss of interest or pleasure in activities that were once enjoyable. Other physical and psychological symptoms include inability to concentrate, motor disturbances (psychomotor retardation or agitation), feelings of worthlessness, inappropriate guilt, thoughts of suicide, and disturbances in appetite and sleep.

Anxiety disorders are a group of syndromes that include generalized anxiety disorder, panic disorder, phobias, obsessive-compulsive disorder, and post traumatic stress disorder. Although each disorder has its own distinct features, all share common symptoms of excessive worrying, intense fears and dread, hypervigilance and/or somatic symptoms, in the absence of a dangerous situation.

Normal sexual function requires, among others, the ability to achieve and maintain penile erection. Major anatomic structures of the penis that are involved in erectile function include the corpus cavernosum, corpus spinosum, and the tunica albuginea (a collagenous sheath that surrounds each corpus). Thecorpora are composed of a mass of smooth muscle (trabecula) which contains a network of endothelial-lined vessels (lacunar spaces). Penile tumescence and erection is caused by relaxation of the arteries and corporal smooth muscles, while closing emissary veins, leading to increased blood flow into the lacunar network. Central and peripheral innervation contributes to regulation of the erectile response.

Erectile dysfunction (ED) may result from failure to initiate, fill, or store adequate blood volume within the lacunar network of the penis. Depending on the underlying dysfunction, ED may be vasculogenic, neurogenic, endocrinologic, diabetic, psychogenic, or medication-related.

ED affects 10-25% of middle-aged and elderly men, and has a profound impact on the well-being of affected men. It is currently treated using PDE5 inhibitors such as vardenafil, tadalifil, and sildenafil. Intraurethral alpostadil (prostaglandin EI) may be used in patients that fail on oral agents. In addition, vacuum constriction devices (VCD) are a well-established, noninvasive therapy.

Female sexual dysfunction (FSD) is highly prevalent, age-related, and progressive. It affects 30 to 50% of women. FSD denotes a range of medical problems and is categorized according to disorders of (1) desire, (2) arousal, (3) orgasm and (4) sexual pain, and symptoms include diminished vaginal lubrication, pain and discomfort with intercourse, decreased arousal, and difficulty achieving orgasm. On a molecular level, vasoactive intestinal peptide (VIP), nitic oxide (NO), and sex hormones such as estrogens and androgens have been suggested to be important in female sexual function. Current treatment approaches include estrogen replacement therapy, methyl testosterone, PDE5 inhibitors such as sildenafil, the NO-donor L-arginine, prostaglandin EI, phentolamine, and the dopamine agonists apomorphine.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilising agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Pharmacological Methods:

I. In-vitro Determination of Affinity to CB1/CB2-Receptors a)

The in-vitro determination of the affinity of the inventive substituted pyrazoline compounds to $CB_1/CB_2$-Rezeptors is carried out as described in the publication of Ruth A. Ross, Heather C. Brockie et al., "Agonist-inverse agonist characterisation at $CB_1$ and $CB_2$ cannabinoid receptors of L-759633, L759656 and AM630", British Journal of Pharmacology, 126, 665-672, (1999), whereby the transfected human $CB_1$ and $CB_2$ receptors of Receptor Biology, Inc. are used. The radioligand used for both receptors is [$^3$H]-CP55940. The respective parts of the description is hereby incorporated by reference and forms part of the present disclosure.

b)

Rat Cerebellum CB1 Binding

Binding affinity to CB1 receptor was evaluated according to a modification of the method described by Govaerts et al., Eur J Pharmac Sci 23, 233-243 (2004). The respective parts of the description is hereby incorporated by reference and forms part of the present disclosure.

Briefly, cerebellum from male wistar rats (250-300 g) were carefully dissected on ice and homogenates were prepared with Potter-Helveheim in a cold 50 mM Tris-HCl solution containing 5 mM $MgCl_2$, 1 mM EDTA and 0-25 M sucrose, pH 7.4. The suspension was centrifuged at 1,000×g for 5 minutes. The supernatants were collected and centrifuged 50,000×g for 15 minutes. The resulting pellets were then resuspended in Tris-HCl buffer without sucrose, homogenized and incubated for 15 min at 37° C. in an orbital shaker bath and centrifuged again at 50,000×g for 15 min. Pellets were weighted, resuspended in Tris-HCl buffer without sucrose, homogenized with Ultraturrax at 13,500 rpm for 3×5 seconds and alicuoted in 0.9 ml volumes in Eppendorf tubes. Alicuotes were centrifuged at 20,800×g for 5 minutes, supernatants discarded and pellets were frozen at −80° C. until use. Total protein concentration was determined using the Bio-Rad Lowry method based kit.

Competitive binding experiments were performed in presence of 1 nM [$^3$H]-CP 55,940 in siliconized glass tubes containing 100 μg protein/tube resuspended in 1 ml final volume of 50 mM Tris-HCl, 5 mM $MgCl_2$, 1 mM EDTA, 0.5% (w/v) bovine serum albumin, pH 7.4. Compounds were present at various concentrations and the non specific binding was determined in the presence of 10 μM HU-210. After 1 hour incubation at 30° C., the suspension was rapidly filtered through 0.5% PEI pretreated GF/B fiber filters on a 96-well harvester and washed 3 times with 3 ml ice-cold binding buffer without bovine serum albumin. Radioactivity on filters was measured with Wallac Winspectral 1414 counter by liquid scintillation in 6 ml Ecoscint H (National Diagnostics, U.K.). Assays were made in triplicates.

Binding data were analyzed by non-linear regression with the software GraphPad Prism Version 3.03.

II. In-vivo Bioassay System for Determination of Cannabinoid Activity

Mouse Tetrad Model

Substances with affinity for cannabinoid receptors are known to produce a wide range of pharmacological effects. It is also known that intravenous administration of a substance with affinity for cannabinoid receptors in mice produces analgesia, hypothermia, sedation and catalepsy. Individually, none of these effects can be considered as proof that a tested substance has affinity for cannabinoid-receptors, since all of these effects are common for various classes of centrally active agents. However, substances, which show all of these effects, i.e. substances that are active in this so-called tetrad model are considered to have affinity for the cannabinoid receptors. It has further been shown that cannabinoid receptor antagonists are highly effective in blocking the effects of a cannabinoid agonist in the mouse tetrad model.

The tetrad model is described, for example, in the publication of A. C. Howlett et al, International Union of Pharmacology XXVII. Classification of Cannabinoid Receptors, Pharmacol Rev 54, 161-202, 2002 and David R. Compton et al., "In-vivo Characterization of a Specific Cannabinoid Receptor Antagonist (SR141716A): Inhibition of Tetrahydrocannbinol-induced Responses and Apparent Agonist Activity", J. Pharmacol. Exp. Ther. 277, 2, 586-594, 1996. The corresponding parts of the description are hereby incorporated by reference.

Material and Methods

Male NMRI mice with a weight of 20-30 g (Harlan, Barcelona, Spain) are used in all of the following experiments.

Before testing in the behavioral procedures given below mice are acclimatized to the experimental setting. Pre-Treatment control values are determined for analgesia hot plate latency (in seconds), rectal temperature, sedation and catalepsy.

In order to determine the agonistic activity of the substance to be tested, the mice are injected intravenously with the substance to be tested or the vehicle alone, 15 minutes after injection, latency in hot plate analgesia is measured.

Rectal temperature, sedation and catalepsy are measured 20 minutes after injection.

In order to determine the antagonistic activity the identical procedure is used as for the determination of the agonistic effects, but with the difference that the substance to be evaluated for its antagonistic activity is injected 5 minutes before the intravenous injection of 1.25 mg/kg Win-55,212 a known cannabinoid-receptor agonist.

Hot Plate Analgesia

The hot plate analgesia is determined according to the method described in Wolf D. et at. "The evaluation of analgesic action of pethidine hydrochloride (Demerol)", J. Pharmacol. Exp. Ther. 80, 300-307,1944. The respective description is hereby incorporated by reference and forms part of the present disclosure.

The mice are placed on a hot plate (Harvard Analgesimeter) at 55±0.5° C. until they show a painful sensation by licking their paws or jumping and the time for these sensations to occur is recorded. This reading is considered the basal value (B). The maximum time limit the mice are allowed to remain on the hot plate in absence of any painful response is 40 seconds in order to prevent skin damage. This period is called the cut-off time (PC).

Fifteen minutes after the administration of the substance to be tested, the mice are again placed on the hot plate and the afore described procedure is repeated. This period is called the post-treatment reading (PT).

The degree of analgesia is calculated from the formula:

$$\% \ MPE \ \text{of Analgesia} = (PT-B)/(PC-B) \times 100$$

MPE=Maximum possible effect.

Determination of Sedation and Ataxia

Sedation and ataxia is determined according to the method described in Desmet L. K. C. et al. "Anticonvulsive properties of Cinarizine and Flunarizine in Rats and Mice", Arzneim.-Forsch. (Frug Res) 25, 9, 1975. The respective description is hereby incorporated by reference and forms part of the present disclosure.

The chosen scoring system is
0: no ataxia;
1: doubtful;
2: obvious calmness and quiet;
3 pronounced ataxia;
prior to as well as after treatment.

The percentage of sedation is determined according to the formula:

$$\% \ \text{of sedation} = \text{arithmetic mean}/3 \times 100$$

Hypothermia:

Hypothermia is determined according to the method described in David R. Compton et al. "In-vivo Characterization of a Specific Cannabinoid Receptor Antagonist (SR141716A) Inhibition of Tetrahydrocannbinol-induced Responses and Apparent Agonist Activity", J. Pharmacol Exp Ther, 277, 2, 586-594, 1996. The respective description is hereby incorporated by reference and forms part of the present disclosure.

The base-line rectal temperatures are determined with a thermometer (Yello Springs Instruments Co., Panlabs) and a thermistor probe inserted to 25 mm before the administration of the substance to be tested. Rectal temperature is again measured 20 minutes after the administration of the substances to be tested. The temperature difference is calculated for each animal, whereby differences of $\geq 2°$ C. are considered to represent activity.

Catalepsy:

Catalepsy is determined according to the method described in Alpermann H. G. et al. "Pharmacological effects of Hoe 249: A new potential antidepressant", Drugs Dev. Res. 25, 267-282. 1992. The respective description is hereby incorporated by reference and forms part of the present disclosure.

The cataleptic effect of the substance to be tested is evaluated according to the duration of catalepsy, whereby the animals are placed head downwards with their kinlegs upon the top of the wooden block.

The chosen scoring system is:

Catalepsy for:
more than 60 seconds=6: 50-60 seconds 5, 40-50 seconds=4, 30-40 seconds=3, 20-30 seconds=2, 5-10 seconds=1, and less than 5 seconds=0.

The percentage of catalepsy is determined according ot the following formula.

$$\% \ \text{Catalepsy} = \text{arithmetic mean}/6 \times 100$$

III. In vivo Testing for Antiobesic Activity
a) Accute Treatment

Normally handled rats were habituated to a reversed cycle 12/12 h, and the tested compound as well as saline was acutely orally administered. After administration the cumulated food intake (g) was measured at 6 h and 24 h. Following that the difference in body weight between control and compound treated animals was measured. This is a variation of the test according to Colombo et al. as described below.

b) Long-term Treatment

The in-vivo testing for antiobesic activity of the inventive pyrazoline compounds is carried out as described in the publication of G. Colombo et al., "Appetite Suppression and Weight Loss after the Cannabinoid Antagonist SR 141716", Life Sciences, 63 (8), 113-117, (1998). The respective part of the description is hereby incorporated by reference and forms part of the present disclosure.

IV. In vivo Testing for Antidepressant Activity

The in-vivo testing for antidepressant activity of the inventive pyrazoline compounds in the water despair test is carried out as described in the publication of E. T. Tzavara et al., "The CB1 receptor antagonist SR141716A selectively increases monoaminergic neurotransmission in the medial prefrontal cortex: implications for therapeutic actions"; Br. J. Pharmacol. 2003, 138(4):544:53. The respective part of the description is hereby incorporated by reference and forms part of the present disclosure.

V. Determination of the Effect of Continued Administration of the Inventive Compounds on Body Weight in Rats The weight of the animals was measured for 36 days, and the data grouped into 3 periods for analysis: Period 1, days 1-8 (period for adaptation of the animals to the environmental conditions: one week without treatment plus first day of treatment); Period 2. days 9-22 (treatment period: two weeks); Period 3, days 23-36 (escape treatment period: two weeks).

The administration of the drugs started on day 8, immediately after the animal was weighted, and finished on day 21. The treatment period ranges between one day after first administration and one day after last administration. The drugs were administered i.p. once daily. For comparative purposes, absolute weights were transformed into relative percentages (each weight was divided by that of day 8 and multiplied by 100). Two treatment groups were constructed: vehicle and (S)-N-piperidinyl-5-(4-chlorophenyl)-1-(2,4-dichlorophenyl)-4,5-dihydro-1H-pyrazole-3-carboxamide (10 mg/kg). The number of animals was 10 for the (S)-N-piperidinyl-5-(4-chlorophenyl)-(2,4-dichlorophenyl)-4,5-dihydro-1H-pyrazole-3-carboxamide group and 9 for the vehicle group. In the vehicle group one animal died whereas in the racemic group one animal was excluded because its weight decreased during 5 days in the post-treatment period. All results are expressed as mean±S.E.M.

The dependence of body-weight (expressed as a percentage relative to day 8) on time (number of lays after inclusion in the study) and treatment was assessed by a two-way (time, treatment) analysis of variance (ANOVA) with repeated measures on the time factor. The analysis was performed on periods 2 and 3, separately, and considering the first or second week in each period. The differences between pairs of curves (treatments) were analyzed using appropriate contrasts within the ANOVA test. The possible interaction between time and treatment was also considered including the Greenhouse-Geisser (G-G) correction. A value of $P<0.05$ was considered significant.

FIG. 1 shows the effect of continued administration (i.p. once daily) of (S)-N-piperidinyl-5-(4-chlorophenyl)-1-(2,4-dichlorophenyl)-4,5-dihydro-1H-pyrazole-3-carboxamide (C) and vehicle on body weight in rats. The S-compound shows a significant action during the treatment period and a relatively fast recovery of weight in the post-treatment period.

VI. In vitro Determination of Antagonism to CB1-Receptor

Membrane Preparation:

Chinese hamster ovary (CHO) cells stably expressing recombinant human cannabinoid 1 receptor (CB1) were cultured in nutrient mixture Ham's F 12 supplemented with 10% heat-inactivated fetal bovine serum, 2 mM L-glutamine, 50 U/ml penicillin, 50 U/ml streptomycin and 0.5 mg/ml geneticin. In order to obtain cells, culture flasks were washed twice with phosphate buffered saline and scraped. Then, cells were collected by centrifugation (200×g, 10 min) and stored dry at −80° C. Cells were homogenized in ice-cold 20 mM HEPES, 10 mM EDTA (pH 7.5) and centrifuged at 40,000×g for 15 min at 4° C. The membrane pellet was resuspended in 20 mM HEPES, 0.1 mM EDTA (pH 7.5) and centrifuged for 15 min at 4° C. The final membrane pellet was resuspended in 20 mM HEPES, 0.1 mM EDTA (pH 7.5), and divided in aliquots and stored at −80° C. until use.

[$^{35}$S]GTPγS Binding Assay:

The reaction was performed in 96-well plates. Membranes (15 µg protein/well) were incubated for 60 min at 30° C. in buffer (50 mM HEPES, 100 mM KCl, 5 mM $MgCl_2$, 1 mM EDTA, 0.1% wt/vol bovine serum albumin, 5 µM GDP, saponin (10 µg/ml), 0.5 nM [$^{35}$S]GTPγS, pH 7.4) with compound at a final concentration of 1 µM in either the absence or presence of agonist WIN 55,212-2 between 3 nM and 3 µM. The incubation was terminated by rapid filtration through Millipore Multiscreen glass fiber FB, and rinsed two-times with ice-cold assay buffer. Filter plates were dried and 30 µl of scintillation liquid was added, Radioactivity was determined using a Wallac Microbeta Trilux. Each experiment was performed at least in duplicate. A WIN 55,212-2 dose-response experiment either alone or in the presence of Rimonabant (1 µM) was systematically performed.

Calculations:

The average of basal [$^{35}$S]GTPγS binding was subtracted from all binding data. In order to compare the antagonism results from one screening campaign to another one, the difference between the maximal agonist effect of WIN 55,212-2 alone, and the maximal antagonism effect due to WIN 55,212-2 plus Rimonabant (1 µM) was defined as 100%.

Further Methods:

Alcohol Intake

The following protocol may be used to evaluate the effects of alcohol intake in alcohol preferring (P) female rats (e.g. bred at Indiana University) with an extensive drinking history. The following reference provides detailed a description of P rats: Lumeng, L, et al., "Different sensitivities to ethanol in alcohol-preferring and-nonpreferring rats," Pharmacol, Biochem Behav., 16, 125-130 (1982).

Female rats are given 2 hours of access to alcohol (10% v/v and water, 2-bottle choice) daily at the onset of the dark cycle. The rats are maintained on a reverse cycle to facilitate experimenter interactions. The animals are initially assigned to four groups equated for alcohol intakes: Group 1-vehicle; Group 2-positive control (e.g. 5.6 mg/kg AM251; Group3-low dose test compound, and Group 4-high dose of test compound. Test compounds are generally mixed into a vehicle of 30% (w/v)—cyclodextrin in distilled water at a volume of 1-2 ml/kg. Vehicle injections are given to all groups for the first two days of the experiment. This is followed by 2 days of drug injections (to the appropriate groups) and a final day of vehicle injections. On the drug injection days, drugs are given sc 30 minutes prior to a 2-hour alcohol access period. Alcohol intake for all animals is measured (luring the test period and a comparison is made between drug and vehicle-treated animals to determine effects of the compounds on alcohol drinking behavior.

Additional drinking studies can be done utilizing female C57Bl/6 mice (Charles River). Several studies have shown that this strain of mice will readily consume alcohol with little to no manipulation required (Middaugh et al., "Ethanol Consumption by C57BU6 Mice: Influence of Gender and Procedural Variables" Alcohol, 17 (3), 175-183, 1999: Le et al., "Alcohol Consumption by C57BL/6, BALA/c, and DBA/2 Mice in a Limited AccessParadigm" PharmacologyBiochemistry and Behavior, 47, 375-378, 1994).

For example, upon arrival mice are individually housed and given unlimited access to powdered rat chow, water and a 10% (wiv) alcohol solution. After 2-3 weeks of unlimited access, water is restricted for 20 hours and alcohol is restricted to only 2 hours access daily. This is done in a manner that the access period was the last 2 hours of the dark part of the light cycle.

Once drinking behavior is stabilized, testing can commence. Mice are considered stable when the average alcohol consumption for 3 days is 20% of the average for all 3 days. Day 1 of test consists of all mice receiving vehicle injection (sc or ip). Thirty to 120 minutes post injection access is given to alcohol and water. Alcohol consumption for that day is calculated (g/kg) and groups are assigned so that all groups have equivocal alcohol intake. On day 2 and 3, mice are injected with vehicle or drug and the same protocol as the previous day is followed. Day 4 iss wash out and no injections are given. Data is analyzed using repeated measures ANOVA. Change in water or alcohol consumption is compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (e.g. 300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i. e., sc, ip, iv). Drugs are prepared in methylcellulose, water or other specified vehicle (examples include PEG400, 30% beta-cyclo dextran and propylene glycol). Oxygen consumption and ambulatory activity are measured every 10 minutes for an additional 1-6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min02 consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption $^{+}$100. Experiments will typically be done with n=4-6 rats and results reported are mean ±SEM.

Interpretation:

An increase in oxygen consumption of >10% is considered a positive result. Historically, vehicle-treated rats have no change in oxygen consumption from pre-dose basal.

Nicotine Dependence

An intravenous nicotine self-administration model or place preference model may be used to assess the effects of a test compound on nicotine dependence (see, e.g., Vastola, et al. Physiol. Behav. 77:107-114, 2002; Brower, et al., Brain Res. 930:12-20, 2002).

Place Preference

Sprague-Dawley rats are used in this study (Vastola, et al., 2002). Animals are housed in a temperature-controlled, 12 h/12 h illumination cycle with ad libitum access to food and water. Conditioning and testing are conducted in a chamber divided into two compartments with a door separating the two compartments. Behavior of the animals is recorded by video camera.

Animals are habituated to the injection procedure for several days. The animals are then placed into the test chamber and given free access to both compartments. The initial preference for a particular compartment is determined. For the conditioning trials, animals are injected with nicotine and restricted to the nonpreferred compartment, or the animals are injected with saline and restricted to the preferred compartment. On test day, the door separating the compartments is removed, the animal is placed in the center of the chamber and allowed to move freely between compartments. Time spent in each compartment is scored. Preferential occupancy of the nicotine compartment follows from the conditioned reinforcing effects of nicotine.

Self-administration

Self-administration in animals is a predictor of a compound's abuse potential in humans. Modifications to this procedure may also be used to identify compounds that prevent or block the reinforcing properties of drags that have abuse potential. A compound that extinguishes the self-administration of a drag may prevent that drag's abuse or its dependence.

Sprague-Dawley rats are used in this study. Initially, animals are housed in a temperature-controlled, 12 h/12 h illumination cycle with ad libitum access to food and water. The animals are then implanted with jugular catheters which exit through the animal's back, and each animal is placed in an individual operant chamber (Brower, et al., 2002). The catheters are connected to a computer-driven syringe pump which is located outside of the chamber. The chamber contains two levers with a green light located above each lever. The light is illuminated when nicotine is available.

In a self-administration test, animals are placed in the operant chambers and the levers are randomly designated as an active and inactive lever. Each response on the active lever produces an infusion of nicotine. Presses on the inactive lever have no effect, but are also recorded. Animals are then trained to self-administer nicotine over a set period of time by having drag access during each daily session. Illumination of the chamber house light signals the beginning of the session and the availability of nicotine. When the session ends, the house light is turned off. Initially, a nicotine infusion occurs with every press of the active lever. Once lever-pressing behavior has been established, the number of presses to produce a nicotine infusion is increased. After stable nicotine self-administration is obtained, the effect of a test compound on the nicotine-reinforced behavior may be evaluated. Administration of this test compound prior to the session can either potentiate, extinguish, or produce no change to the self-administrating behavior. Tests are conducted every two days, and the order of the administration of the test compound doses is controlled.

Alzheimer/Dementia Experiments

Morris Water Maze Task

The Morris water maze is a behavioral in vivo test to measure spatial orientation learning and memory through a complex learning task. It is highly suitable for testing compounds that enhance learning and memory. A circular water tank or pool (diameter 2 m, height 0.7 m) is filled with water, and a 10 cm2 platform is placed 1-1.5 cm below the water surface at a defined location within the pool. The escape platform is not visible for an animal swimming in the water tank. For the experiment, a rat or mouse is placed into the pool to swim freely.

The animals have the task to localize the submerged platform, and the time and distance required for successful retrieval is measured. Multiple extra-maze cues are provided by the furniture in the room, including desks, computer equipment, a second water tank, the presence of the experimenter, and by a radio on a shelf that is playing softly.

Before administration of the test compound, animals are usually trained in the task 4 times a day for 5 days. Test compounds are administered orally or intraperitoneally on the day of the experiment at a defined time (e.g., 30 minutes before the first swim test). Control animals are dosed with the corresponding vehicle not containing test compound. Active compounds yield shorter times and distances to localize the platform (i.e., the better the animal remembers the location of the platform the shorter the distance covered and the faster the platform is reached).

The test can also be carried out using transgenic or cognitively impaired animals. Cognitive impairment is induced either by old age or experimentally through brain lesions, such as bilateral lesions of the entorhinal cortex in rats, Such lesions can be induced by intracerebral injections of the excitotoxin ibotenic acid.

Object Recognition Task

The object recognition task is used to assess the effects of compounds on the cognitive performance of rodents. A rat is placed in an open field, in which two identical objects are located. The rats inspects both objects during the initial trial of the test. After a certain retention interval (e.g., 24 hours), a second trial is carried out. Here, one of the two objects used in the first trial (the 'familiar' object) and a novel object are placed in the open field, and the inspection time at each or the objects is measured. Good retention is reflected by higher exploration times towards the novel compared with the 'familiar' object.

Administration of the putative cognition enhancer prior to the first trial predominantly allows assessment of the effects on acquisition, and on the consolidation processes. Administration of the test compound after the first trial allows to assess the effects on consolidation processes, whereas administration before the second trial allows to measure effects on retrieval processes.

Passive Avoidance Task

The passive avoidance task assesses memory performance in rats and mice. The inhibitory avoidance uses an apparatus consisting of a box with two compartments separated by a guillotine door that can be operated by the experimenter. One compartment is illuminated with bright light, and the other compartment is dark. A threshold of 2 cm separates the two compartments when the guillotine door is 15 raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. During the habituation sessions and the retention session, the rat is allowed to explore the apparatus for 300 seconds. The rat is placed in the light compartment, facing the wall opposite to the guillotine door. After an accommodation period of 15 seconds, the guillotine door is opened so that all parts of the apparatus can be visited freely. Rats normally avoid brightly lit areas and will enter the dark compartment within a few seconds.

In the shock session, the guillotine door between the compartments is lowered as soon as the rat has entered the dark compartment with all paws, and a scrambled 1 mA footshock is administered for 2 seconds. Then the rat is removed from the apparatus and returned into its home cage. The procedure during the retention session is identical to that of the habituation sessions.

The step-through latency, that is, the first latency of entering the dark compartment (in seconds) during the retention session is an index of the memory performance of the animal: a better retention is assumed if the latency to enter the dark compartment is longer. A test compound is given 30 minutes before the shock session, together with 1 mg/kg scopolamine. Scopolamine impairs the memory performance during the retention session 24 hours later. If the test compound increases the enter latency compared with the scopolamine-treated controls, it is considered to possess cognition enhancing activity. T-maze Spontaneous Alternation Task The T-maze spontaneous alternation task (TeMCAT) assesses the spatial memory performance in mice. The start arm and the two goal arms of the T-maze are provided with guillotine doors that can be operated manually by the experimenter. A mouse is put into the start arm at the beginning of training. In the first trial, either the left or right goal arm is blocked by lowering the respective guillotine door (forced trial).

After the mouse has been released from the start arm, it will explore the maze, eventually entering the open goal arm, and return to the start position, where it will be confined for 5 seconds, by lowering the guillotine door. Then, the animal can choose freely between the left and right goal arm (all guillotine-doors opened) during 14 additional trials (free choice trials). As soon as a mouse has entered one goal arm, the other arm is closed. The mouse eventually returns to the start arm and is free to visit whichever arm it wants after having been confined to the start arm for 5 seconds. After completion of 14 free choice trials in one session, the animal is removed from the maze.

Out of the 14 trials the alternations in percent are calculated. This percentage and the total time needed to complete the first forced trial and the subsequent 14 free choice trials (in seconds) is analyzed. In addition, cognitive deficits can be induced by injection of scopolamine 30 minutes before the start of the training session. A cognition enhancer, administered before the training session, will at least partially, antagonize the scopolamine-induced reduction in the spontaneous alternation rate.

Depression Model

A forced swim or tail suspension model may be used to assess the efficacy of antidepressant compounds (see , e.g. Porsolt, et al., Nature 266:730-732, 1977: Stem, et al., Psychopharmacology 85:367-370, 1935).

Forced Swim Test

Rats or mice are placed in a cylinder filled with water 23-25° C. from which no escape is possible. Initially, animals struggle and try to escape, but eventually adopt a characteristic immobile posture and make no further attempts to escape except for small movements needed their head above water. Animals are dosed with a compound and the activity (swimming or climbing) or immobility is measured by an observer. The immobility is considered by some to reflect a 'behavioral despair' in which animals cease to struggle to escape the aversive situation. A wide variety of clinically used antidepressants (TCAs, MAOIs, SSRIs, atypicals) decrease immobility in this test and has a good predictive validity in that it detects antidepressants with different mechanisms of action but its construct validity is weak. At least two distinct active behavioral patterns are produced by pharmacologically selective antidepressant drugs. Serotonin-selective reuptake inhibitors increase swimming behavior, whereas drugs acting primarily to increase extracellular levels of norepinephrine or dopamine increase climbing behavior. There are false positives (psychostimulants) but relatively few false negatives ([beta]-adrenergic agonists). The test is sensitive to muscle-relaxant (benzodiazepines) and sedative (neuroleptics) effects, leading to enhanced immobility, False positives and false negatives can often be screened by measuring if the compound produces locomotor stimulation or sedation.

Tail Suspension Test

When suspended by the tail, mice will initially struggle and try to escape and then alternate between active escape attempts and immobililty. In this test, animals are dosed with a compound and the immobility is measured by an observer for 6 min. Porsolt describes the immobile behavior as 'behavioral despair' which animals cease to struggle to escape the aversive situation A large variety of clinically antidepressants (tricyclics, MAOIs, SSRIs, and atypicals) reduce immobility in this model. The test has a good predictive validity for antidepressant activity and works for most antidepressant classes including but has some false positives (psychostimulants.) The test is sensitive to muscle-relaxant (benzodiazepines) and sedative (neuroleptics) effects, which lead to enhanced immobility. False positives and false negatives can often be screened by measuring if the compound produces locomotor stimulation or sedation. Strain differences in the tail suspension test have been found in mice. The tail suspension test has some face validity but its construct validity is rather weak.

Schizophrenia Model

A prepulse inhibition model may be used to assess the efficacy of antipsychotic compounds (see Swerdlow and Geyer, Schizophrenia Bulletin 24: 285-301, 1998).

Prepulse Inhibition

Prepulse inhibition is the process whereby a relatively mild stimulus, the prepulse, suppresses the response to a strong, startle-eliciting stimulus when the prepulse precedes the startle stimulus by a brief duration (about 10 to 500 milliseconds). Prepulse inhibition is a cross-species phenomenon (ie, it is present in mammals ranging from mice to humans), yet it is relatively absent among schizophrenic patients. The deficit in PPI in schizophrenic patients is thought to reflect the loss of sensorimotor gating that may lead to sensory flooding and cognitive fragmentation. In this test, mice or rats are administered compounds and individually placed into a holder on a transducer platform to measure whole body startle. The holder is housed in a startle chamber with background white noise. Following a brief habituation period, animals are given multiple trials of a weak auditory prepulse stimulus, followed by a strong auditory startle stimulus. Four types of trials are given: prepulse plus startle, prepulse alone, startle alone, and no stimulation PPI is measured as the amount of inhibition of startle following the prepulse and is expressed as the percentage of basic startle. As a control, measurements are taken in the no stimulation and prepulse alone trials. PPI is considered a test with good predictive, face and construct validity for schizophrenia. Putative antipsychotics can be tested alone to determine if they enhance PPI. Alternately, antipsychotics can be screened to determine if they block various agents that disrupt PPI (apomorphine. d-amphetamine, PCP, ketamine, DOI). Finally, mutant mice with or without drugs can be screened using the PPI procedure.

Anxiety Model

An elevated plus maze model may be used to assess the efficacy of anxiolytic compounds (see Pellow and File, Pharm. Biochem. Behav. 24, 525-529, 1986).

Elevated Plus Maze

The elevated plus maze is widely used as an anxiety paradigm that examines the conflict between the drive to explore and the aversiveness of heights and open spaces of rats or mice. The maze is a cross made up of two open and two closed arms that is raised above the ground. The combination of light, the open arms, and the height is thought to produce unconditioned fear or anxiety responses in mice or rats, The test apparatus is an open top maze constructed of opaque plastic with alternating open and enclosed arms. For rats, each arm is 45-55 cm long and 8-12 cm wide, with the sides of the enclosed arms 35-45 cm high, the juncture approximately 10×10 cm, and the maze is elevated 45-55 cm above the floor. The mouse elevated plus maze consists of two closed arms (15×6×30 cm) and two open arms (1×6×30 cm) forming a cross, with a quadrangular center (6×6 cm). The maze is placed 50 cm above the floor. Testing is performed in a room free of noise and distraction. On test days animals are administered drug or vehicle. If a pretreatment period is necessary, the animals are returned to the home cage for the duration of the pretreatment time; otherwise, the animals are placed in a clear plastic holding chamber singly or with cage mates for 1-10 minutes prior to test time. Rats are then placed in the center of the maze always oriented in the same direction, either consistently facing an open arm or an enclosed arm. For 5-10 minutes, entries into each arm and the time spent in each arm are recorded by the observer(s) or by videotape or a computer receiving input from a video camera mounted above the maze. To count as an entry, all four paws must be inside the arm, if necessary, additional measures of anxiety-related behaviors will be recorded, i.e., time spent motionless, time spent in the center, time spent grooming, and the number of rears, stretching postures or feces produced. Following testing the animals are returned to the home cages. When animals are placed in the center of the maze, they spend most of their time in the closed arms, avoiding the open arms. Anxiolytic drugs, such as benzodiazepines, will increase the amount of time animals spend in the open arms. The test is also sensitive to anxiogenic drugs, which lends strong support for its predictive validity.

Erectile Dysfunction

Drugs affecting erectile function may be tested by measuring the effect on apomorphine-evoked increases in intracavernous pressure in the awake rat as described by Andersson. et al., (J. Urol. 161 : 1707-17] 2. 1999). One end of a polyethylene tubing is implanted into the cavernosal space of the penis of male Sprague-Dawley rats. After recovery from the surgery, intracavernous pressure is recorded using a pressure transducer connected to a multichannel pen-recorder. Erections are induced by administration of apomorphine (100-250 ug/kg s.c.) with or without test compound, and the results are compared for the treated group and the non-treated group.

Female Sexual Dysfunction

Systems to test compounds for the treatment of female sexual dysfunction include in vitro and in situ models using vaginal or clitoral smooth muscle preparations, histological evaluation, and vaginal blood flow assessments. In vivo studies of sexual responses focus on behavioral paradigms involving lordotic posturing and receptivity, as well as indices of motivation using a dual chamber pacing method (see, e.g., Hale, et al., Int. J. Impot. Res. 15 Suppl 5: S75-79, 2003).

The present invention is illustrated below with the aid of examples. These illustrations are given solely by way of example and do not limit the general spirit of the present invention.

EXAMPLES

Abbreviations:

Eq. Equivalent

Proc. Process

Solv. Cryst. Solvent used in crystallisation experiment

T Cryst. Temperature at which crystallisation experiment was carried out $1^{st}$ Cryst. First crystallisation $2^{nd}$ Crys. Second crystallisation r.t. room temperature ($\approx$20-25° C.)

Example 1

General synthesis of racemic N-piperidinyl-5-(4chlorophenyl)-1-(2,4-dichlorophenyl)-4,5-dihydro-1H-pyrazole-3-carboxamide a) 4-(4-chlorophenyl)-2-oxo-3-butenoic acid

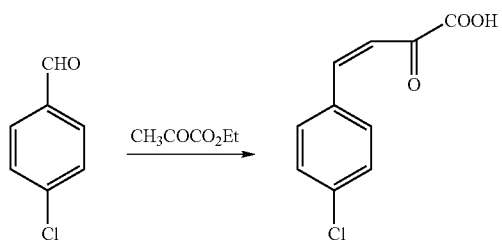

In a three neck flask p-chlorobenzaldehyde (13.3 g, 95 mmoles) and ethyl pyruvate (10 g, 86 mmoles) were dissolved in 150 ml of absolute ethanol. The solution was ice-cooled to 0° C. and an aqueous solution of NaOH (3.8 g in 45 mL water) was added dropwise keeping the temperature below or equal to 10° C., whereby a yellow-orange colored precipitate was formed The reaction mixture was stirred for 1 hour at 0° C. and an additional 1.5 hours at room temperature (approximately 25° C.), Afterwards the reaction mixture was cooled down to approximately 5° C. and the insoluble sodium salt of 4-(4-chlorophenyl)-2-oxo-3-butenoic acid was isolated by filtration.

The filtrate was left in the refrigerator overnight, whereby more precipitate is formed, which was filtered off, combined with the first fraction of the salt and washed with diethyl ether. The sodium salt of 4-(4-chlorophenyl)-2-oxo-3-butenoic acid was then treated with a solution of 2N HCl, stirred for some minutes and solid 4-(4-chlorophenyl)-2-oxo-3-butenoic acid was separated via filtration and dried to give 12.7 g of the desired product (70% of theoretical yield).

IR (KBr, cm$^{-1}$): 3500-2500, 1719.3, 1686.5, 1603.4, 1587.8, 1081.9.

$^1$H NMR(CDCl$_3$, δ): 7.4 (d, J=8.4 Hz, 2H), 7.5 (d, J=16.1 Hz, 1H), 7.6 (d, J=8.4 Hz, 2H), 8.1(d, J=16.1 Hz, 1H).

b) 5-(4-chlorophenyl)-1-(2,4-dichlorophenyl)-4,5-dihydro-pyrazole-3-carboxylic acid

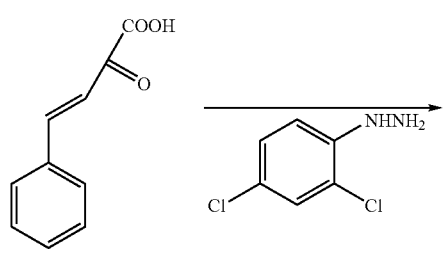

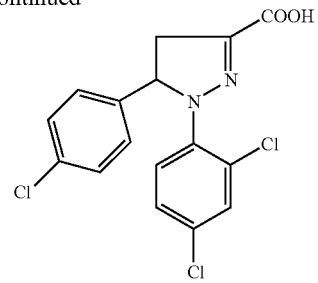

4-(4-chlorophenyl)-2-oxo-3-butenoic acid obtained according to step a) (12.6 g, 60 mmoles), 2,4-dichlorophenylhydrazine hydrochloride (12.8 g, 60 mmoles) and glacial acetic acid (200 mL) were mixed under a nitrogen atmosphere and heated to reflux for 4 hours, cooled down to room temperature (approximately 25° C.) and given into ice-water, whereby a sticky mass was obtained, which was extracted with methylene chloride. The combined methylene chloride fractions were washed with water, dried with sodium sulfate, filtered and evaporated to dryness to give a pale yellow solid (12.7 g, 57% of theoretical yield).

IR (KBr, cm$^{-1}$): 3200-2200, 1668.4, 1458, 1251.4, 1104.8.

$^1$H NMR (CDCl$_3$, δ): 3.3 (dd, 1H), 3.7 (dd, 1H), 5.9 (dd, 1H), 7.09-7.25 (m, 7H).

c) 5-(4-chlorophenyl)-1-(2,4-dichlorophenyl)-4,5-dihydro-pyrazole-3-carboxylic acid chloride

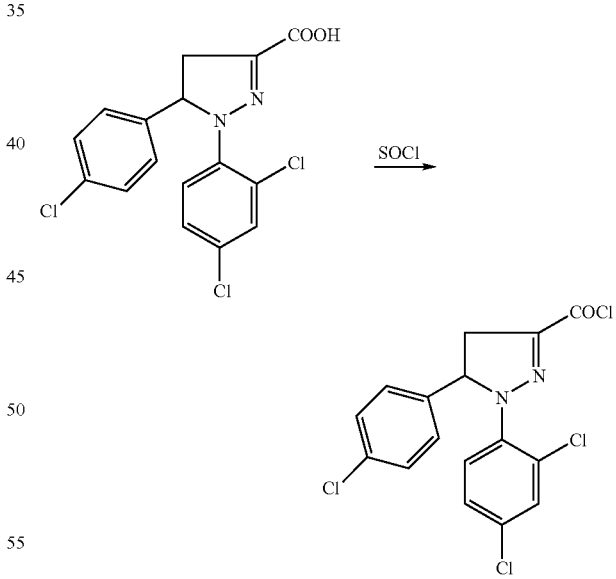

Under nitrogen atmosphere 5-(4-chlorophenyl)-1-(2,4-dichlorophenyl)-4,5-dihydro-pyrazole-3-carboxylic acid (2.5 g, 6.8 mmols) obtained according to step (b) was dissolved in 4 mL of in thionyl chloride and heated to reflux for 2.5 hours. The excess thionyl chloride is removed from the reaction mixture under reduced pressure and the resulting crude residue (2.6 g) is used without any further purification.

IR (KBr, cm$^{-1}$): 1732.3, 1700, 1533.3, 1478.1, 1212.9, 826.6.

d) N-piperidinyl-5-(4-chlorophenyl)-1-(2,4-dichlorophenyl)-4,5-dihydropyrazole-3-carboxamide

[this compound may also be referred to as 5-(4-Chloro-phenyl)-1-(2,4-dichloro-phenyl)-4,5-dihydro-1H-pyrazole-3-carboxylic acid piperidin-1-ylamide or as 1-(2,4dichlorophenyl)-5-(4-chlorophenyl)-4,5-dihydro-N-(piperidin-1-yl)-1H-pyrazole-3-carboxamide]

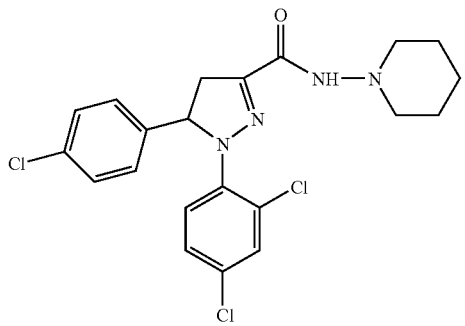

Under nitrogen atmosphere N-aminopiperidine (0.6 mL, 5.6 mmoles) and triethylamine (4 mL) were dissolved in methylene chloride (25 mL). The resulting mixture was ice-cooled down to 0° C. and a solution of 5-(4-chlorophenyl-1-(2,4-dichlorophenyl)-4,5-dihydro-pyrazole-3carboxylic acid chloride obtained in step (c) in methylene chloride (15 mL) was added dropwise. The resulting reaction mixture was stirred at room temperature (approximately 25° C.) overnight. Afterwards the reaction mixture was washed with water, followed by a saturated aqueous solution of sodium bicarbonate, then again with water, dried over sodium sulfate, filtered and evaporated to dryness in a rotavapor. The resulting crude solid was crystallized from ethanol. The crystallized solid was removed via filtration and the mother liquors were concentrated to yield a second fraction of crystallized product. The two fractions were combined to give a total amount of 1.7 g (57% of theoretical yield) of N-piperidinyl-5-(4-chlorophenyl)-1-(2,4-dichlorophenyl)-4,5-dihydropyrazole-3-carboxamide having a melting point of 183-186° C.

IR (KBr, cm$^{-1}$): 3222.9, 2934.9, 1647.4, 1474.7, 1268.3, 815.6.

$^1$H NMR (CDCl$_3$, δ): 1.4 (m, 2H), 1.7 (m, 4H), 2.8 (m, 4H), 3.3 (dd, J=6.1 y 18.3 Hz, 1H), 3.7 (dd, J=12.5 and 18.3 Hz, 1H), 5.7 (dd, J=6.1 and 12.5 Hz, 1H), 7.0-7.2 (m, 6H), 7.4 (s, 1H).

The resolution of the racemate of N-piperidinyl-5-(4-chlorophenyl)-1-(2,4-dichlorophenyl)-4,5-dihydro-1H-pyrazole-3-carboxamide may be carried out by methods known to those skilled in the art, e.g. column chromatography.

However, is has been found by the present inventors that its intermediate, namely racemic 5-(4-chlorophenyl)-1-(2,4-dichlorophenyl)-4,5-dihydro-pyrazole-3-carboxylic acid may easily be separated into the respective enantiomers via reaction with a chiral base. The process for this resolution is described below.

Example 2

Resolution of the enantiomers of 5-(4-chlorophenyl)-1-(2,4-dichlorophenyl)-4,5-dihydro-pyrazole-3-carboxylic acid The resolution of the enantiomers of 5-(4-chlorophenyl)-1-(2,4-dichlorophenyl)-4,5-dihydro-pyrazole-3-carboxylic acid was carried out via reaction with the following chiral bases:

Brucine
Quinine
(−)-Cinchonidine
(+)-Cinchonine
R-(+)-1-Phenylethylamine
(1R,2S)-(−)-Ephedrine hydrochloride
(1S,2R)-(+)-Ephedrine hydrochloride.

In each case the reactions were carried out with 0.5 and 1 equivalents of base in respect to 1 equivalent of the acid compound and by using the following solvents Ethanol
Acetone
Acetonitril
Dioxane
Ethylacetate
Chloroform.

The results are summarized in the following tables, It may be understood that the afore mentioned crystallisation experiments that are not reflected in the following tables did not yield crystals of the respective salts under the given conditions.

However, suitable conditions for crystallization of these salts can be determined by those skilled in the art via routine experiments.

In the following tables

Acid represents racemic 5-(4-chlorophenyl)-1-(2,4-dichlorophenyl)-4,5-dihydro-pyrazole-3-carboxylic acid R-Acid represents the respective derivative of (R)-5-(4-chlorophenyl)-1-(2,4-dichlorophenyl)-4,5-dihydro-pyrazole-3-carboxylic acid S-Acid represents the respective derivative of (S)-5-(4-chlorophenyl)-1-(2,4-dichlorophenyl)-4,5-dihydro-pyrazole-3carboxylic acid Processes for Crystallisation:

Process A: A solution of the chiral base was added on top of a solution of the racemic acid at room temperature, Process C: A solution of the racemic acid was added on top of a solution of the chiral base. The mixture was heated to reflux and solvent was added until dissolution was complete, The solution was left to crystallisation at r.t.

Process D: The chiral base was directly added on top of a solution of the racemic acid at room temperature.

Process E: The chiral base was directly added on top of a solution of the racemic acid at reflux temperature.

Process F: The solution of the salt was evaporated to dryness. The residue was dissolved in a minimum amount of the solvent under reflux heating. The solution was left to crystallisation at r.t.

Resolution with Brucine

Brucine

| Acid g (mmol) | Eq. amine | Proc. | Solvent for crystallisation | T Cryst. | Yield 1st Cryst. % | % S-Acid | % R-Acid | Yield 2nd Cryst. % | % S-Acid |
|---|---|---|---|---|---|---|---|---|---|
| 0.4 g (1.09 mmol) | 0.5 | A | 8 ml acetone | r.t | 44.6 | 98.8 | 1.2 | 5.6% | 99.4 |
| 0.4 g (1.09 mmol) | 0.5 | A | 11.5 ml acetonitrile | r.t. | 50.7 | 47.5 | 52.4 | | |
| 0.4 g (1.09 mmol) | 1 | A | 17 ml acetonitrile | r.t. | 25.6 | 45.7 | 54.3 | | |

Resolution with Quinine

| Acid g (mmol) | Eq. amine | Proc. | Solvent for crystallisation | T Crys. | Yield 1st Cryst. % | % S-Acid | % R-Acid |
|---|---|---|---|---|---|---|---|
| 0.4 g (1.09 mmol) | 1 | A | 8 ml dioxane | r.t. | 49.46 | 91.6 | 8.3 |
| 0.4 g (1.09 mmol) | 1 | F | 15 ml acetonitrile | r.t. | 26 | 94.4 | 5.5 |
| 0.4 g (1.09 mmol) | 1 | F | 2 ml ethyl-acetate | r.t. | 25 | 96.7 | 3.3 |
| 0.4 g (1.09 mmol) | 0.5 | A | 4 ml dioxane | r.t. | 38.5 | 97.5 | 2.5 |

Resolution with (−)-Cinchonidine

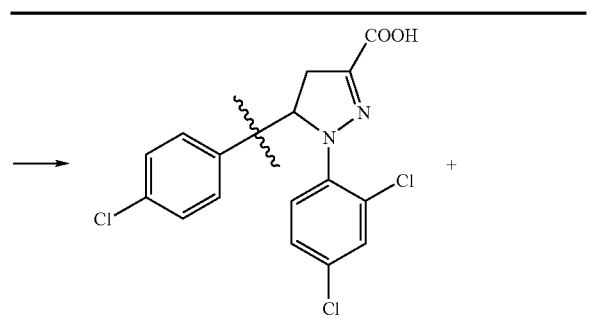

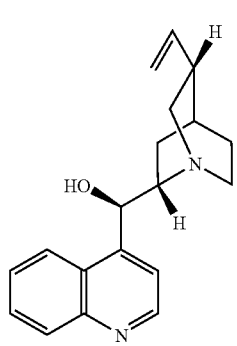

| Acid g (mmol) | Eq. amine | Proc. | Solvent for crystallisation | T Cryst. | Yield 1st Cryst. % | % S-Acid | % R-Acid |
|---|---|---|---|---|---|---|---|
| 0.4 g (1.09 mmol) | 1 | F | 2 ml dioxane | r.t. | 31 | 94.4 | 5.6 |
| 0.4 g (1.09 mmol) | 1 | F | 19 ml Ethylacetate | r.t. | 28.5 | 95.8 | 4.2 |
| 0.4 g 1.09 mmol | 1 | F | 20 ml acetone | r.t. | 19.6 | 96.9 | 3.1 |
| 0.4 g (1.09 mmol) | 1 | F | 24 ml acetonitrile | r.t. | 42 | 85.8 | 14.1 |

Resolution with (+)-Cinchonine

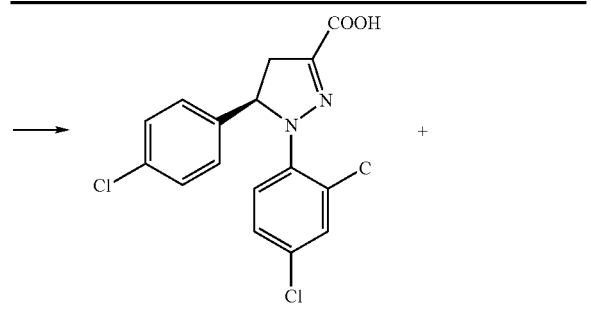

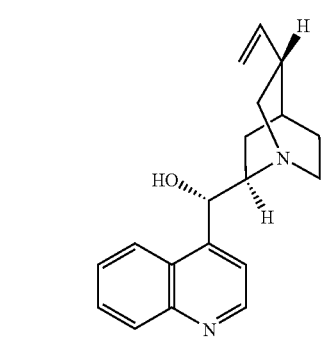

| Acid | Eq. amine | Proc. | Solvent for crystallisation | T Cryst. | Yield 1st Cryst. % | % S-Acid | % R-Acid |
|---|---|---|---|---|---|---|---|
| 0.4 (1.09 mmol) | 1 | C | 50 ml acetone | r.t. | 32.8 | 7.42 | 92.57 |
| 0.4 (1.09 mmol) | 0.5 | F | 30 ml acetone | r.t. | 23.5 | 4.0 | 95.9 |
| 0.4 (1.09 mmol) | 0.5 | C | 50 ml acetonitrile | r.t. | 31.5 | 3.07 | 96.92 |
| 0.4 (1.09 mmol) | 1 | C | 50 ml acetonitrile | r.t. | 78.25 | 39.01 | 60.98 |
| 0.4 (1.09 mmol) | 0.5 | C | 15 ml ethylacetate | r.t. | 14.9 | 3.62 | 96.37 |
| 0.4 (1.09 mmol) | 1 | C | 27 ml ethylacetate | r.t. | 35 | 7.78 | 92.21 |
| 0.4 (1.09 mmol) | 1 | F | 4 ml dioxane | r.t. | 21 | 33.5 | 66.4 |

Resolution with R-(+)-1-Phenylethylamine

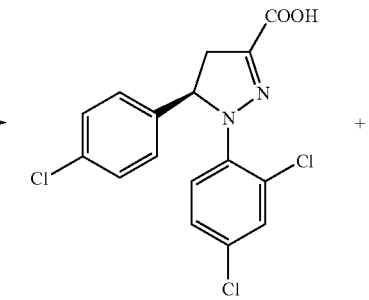

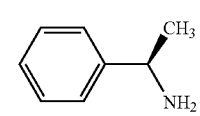

| Acid | Eq. amine | Proc. | Solvent for crystallisation | T Cryst. | Yield 1st Cryst. % | % S-Acid | % R-Acid |
|---|---|---|---|---|---|---|---|
| 0.4 (1.09 mmol) | 1 | D | 1.6 ml etanol | r.t. | 22 | 51.4 | 48.6 |

-continued

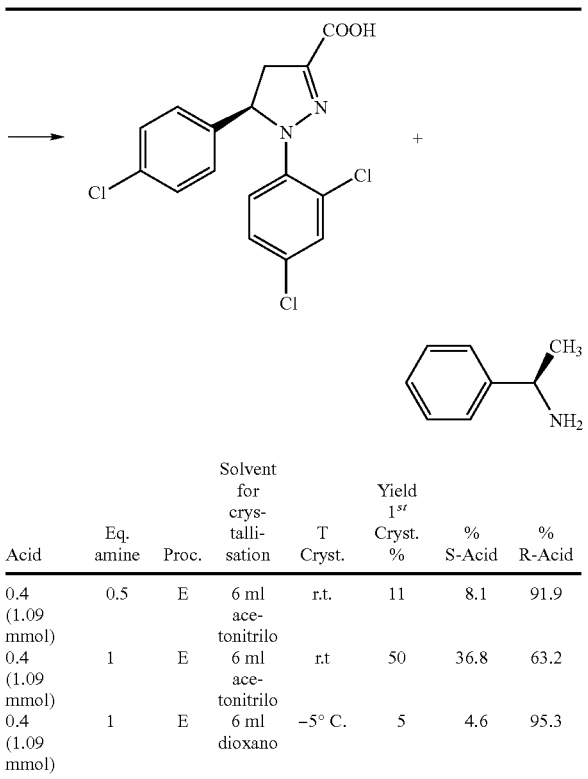

| Acid | Eq. amine | Proc. | Solvent for crystallisation | T Cryst. | Yield 1st Cryst. % | % S-Acid | % R-Acid |
|---|---|---|---|---|---|---|---|
| 0.4 (1.09 mmol) | 0.5 | E | 6 ml acetonitrilo | r.t. | 11 | 8.1 | 91.9 |
| 0.4 (1.09 mmol) | 1 | E | 6 ml acetonitrilo | r.t | 50 | 36.8 | 63.2 |
| 0.4 (1.09 mmol) | 1 | E | 6 ml dioxano | −5° C. | 5 | 4.6 | 95.3 |

Detailed Description

Resolution of 5-(4-chlorophenyl)-1-(2,4-dichlorophenyl)-4,5-dihydro-pyrazole-3-carboxylic acid with (+)-Cinchonine 35 g (294.68 mmol) of racemic 5-(4-chlorophenyl)-1-(2,4-dichlorophenyl)-4,5-dihydro-pyrazole-3-carboxylic acid in 630 m acetonitril were added to a suspension of 16.39 g (47.34 mmol) of (+)-Cinchonine in 920 ml acetonitrile under vigorous stirring. The resulting suspension was heated to reflux and acetonitrite (1300 ml) was addend until dissolution was complete. The resulting solution was left to crystalize at room temperature over the weekend, whereupon a crystalline solid was obtained. The crystalline solid was filtered off, washed with 50 ml of cold acetonitrile and dried to give 25.26 g of a white solid (ee≈91-92%). No second fraction of crystals could be obtained from the, mother liquors, neither upon cooling in the refrigerator nor upon concentration. Thus, recrystallisation of the diastereomeric salt was carried out in different solvents in order to improve the enantiomeric excess:

| Solvent | Yield | ratio of enantiomers % (R)/% (S) |
|---|---|---|
| Acetonitrile | 90% | 99.6/0.4 |
| EtOH—H$_2$O | 68.5% | 99.3/0.7 |
| Isopropanol | 55% | 98.9/1.1 |

Consequently, the product was recrystallized from acetonitrile to give 22.6 g of crystals (yield 72 mol-% related to chiral base). The ratio of enantiomers determined by capilar electrophoresis was:

99.7% of (R)-5-(4-chlorophenyl-1-(2,4-dichlorophenyl)-4,5-dihydro-pyrazole-3-carboxylic acid (+)-Cinchonine
0.3% of (S)-5-(4-chlorophenyl)-1-(2,4-dichlorophenyl)-4,5-dihydro-pyrazole-3-carboxylic acid (+)-Cinchonine
ee=99.4%.

Preparation of (R)-5-chlorophenyl)-1-(2,4-dichlorophenyl)-4,5-dihydro-pyrazole-3-carboxylic acid from addition compound (R)-5-(4chlorophenyl)-1-(2,4-dichlorophenyl)-4,5-dihydro-pyrazole-3-carboxylic: acid-(+)-Cinchonine 22.59 g (34 mmol) of the diastereomeric salt, which was recrystallized from acetonitrile, were suspended in 200 ml of 6N HCl and stirred at room temperature for 15 minutes. Afterwards, 200 ml of toluene were added until dissolution was complete. The mixture was stirred for 30 minutes and the phases were separated. The aqueous phase was extracted with toluene, the combined organic phases were washed with water, dried over sodium sulfate, filtered and evaporated to dryness, whereupon 11.9 g (95%) of a white microcrystalline solid (melting point 129-133) were obtained.

Enantiomeric excess determined by capilar electrophoresis. ee=99.2%
Chemical purity determined by HPLC: 99.3%
$[\alpha]_D$ (c=1.23° C., MeOH)=−429.

Isolation of the Enantiomer (R)-5-(4-chlorophenyl)-1-(2,4-dichlorophenyl)-4,5-dihydro-pyrazole-3-carboxylic acid from the Mother Liquors Obtained from the crystallisation of the Enantiomer (S)-5-(4chlorophenyl)-1-(2,4-dichlorophenyl)-4,5-dihydro-pyrazole-3-carboxylic acid with Brucine The residue obtained from the evaporation of the mother liquors obtained from the crystallisation of (S)-5-(4-chlorophenyl)-1-(2,4-dichlorophenyl)-4,5-dihydro-pyrazole-3-carboxylic acid with Brucine was treated with EN HCl as described above for obtaining the free acid. After evaporating the organic phase 21.86 g of a mixture with a theoretical composition of 20 mmoles (S)-5-(4-chlorophenyl)-1-(2,4-dichlorophenyl)-4,5-dihydro-pyrazole-3-carboxylic acid and 39.9 mmoles of (R)-5-(4-chlorophenyl)-1-(2,4-dichlorophenyl)-4,5-dihydro-pyrazole-3-carboxylic acid were obtained. A suspension of 13.82 g (39.9 mmoles) of (+)-cinchonine in 1000 ml of acetonitrile were added and the mixture was heated to reflux. More acetonitrile was added until dissolution was complete (total volume of acetonitrile 4000 ml). The mixture was then slowly cooled to room temperature to obtain crystals. After a few hours a white solid was obtained, which was filtered off and dried to give 22.42 (yield 84.5% related to the salt of (R)-5-(4-chlorophenyl)-1-(2,4dichlorophenyt)-4,5-dihydro-pyrazole-3-carboxylic acid).

Enantiomeric excess as determined by capilar electrophoresis was ee=92%.

The purity of the isolated salt was comparable to the one of the salt obtained directly from the resolution of the racemate. Consequently, the same purification process as described above could be applied.

Resolution of racemic S-(4-chlorophenyl)-1-(2,4-dichlorophenyl)-4,5-dihydro-pyrazole-3-carboxylic acid with Brucine Preparation of the diastereomeric salt with Brucine
At room temperature 15.74 g (39.9 mmol) of Brucine were dissolved in 475 ml of acetone under vigorous stirring. A solution of 29.5 g (79.8 mmol) of the racemic 5-(4-chlorophenyl)-1-(2,4-dichlorophenyl)-4,5-dihydro-pyrazole-3-carboxylic acid in 85 ml acetone was added. The resulting mixture was allowed to crystallize for a couple of days, whereupon a crystalline solid was obtained. The crystalline solid was filtered off, washed with cold acetone and dried to yield 13.66 g (45 mol % related to the base) of a beige-coloured solid were obtained.

The ratio of the enantiomers as determined by capilar electrophoresis was:

99% of (S)-5-(4-chlorophenyl)-1-(2,4-dichlorophenyl)-4,5-dihydro-pyrazole-3-carboxylic acid Brucine 1% of (R)-5-(4-chlorophenyl)-1-(2,4-dichlorophenyl)-4,5-dihydro-pyrazole-3-carboxylic acid Brucine Enantiomeric, excess ee=98%

The filtered mother liquors were left in the refrigerator and yielded a second fraction of crystals, which were filtered off and dried to give another 1.56 g (5.1 molar % related to the base).

The analysis of the $2^{nd}$ fraction via capillar electrophoresis gave 99.3%, of (S)-5-(4-chlorophenyl)-1-(2,4-dichlorophenyl)-4,5-dihydro-pyrazole-3-carboxylic acid Brucine 0.7% of (R)-5-(4-chlorophenyl)-1-(2,4-dichlorophenyl-4,5-dihydro-pyrazole-3-carboxylic acid Brucine Enantiomeric excess ee=98.6%

Total yield:

15.22 g (50.1 mol % related to base) of the sal with ee=98%.

Determination of the Chirality of the Brucine Salt via X-ray Crystallography

The chirality of the enantiomer that crystallized with Brucine (ee 98%) was determined via x-ray crystallography and corresponds to the S-enantiomer. Accordingly, the other enantiomer that crystallized with (+)-cinchonine is the corresponding R-enantiomer.

Preparation of (S)-5-(4-chlorophenyl)-1-(2,4dichlorophenyl)-4,5-dihydro-pyrazole-3-carboxylic acid from Addition Compound (S)-5-(4chlorophenyl)-1-(2,4dichlorophenyl)-4,5-dihydro-pyrazole-3-carboxylic acid Brucine 15.17 g (19.85 mmol) of (S)-5-(4-chlorophenyl)-1-(2,4-dichlorophenyl)-4,5-dihydro-pyrazole-3-carboxylic acid Brucine were suspended in 150 ml of 6N HCl and the suspension was stirred for 10 minutes, followed by the addition of 150 ml of toluene upon which complete dissolution was observed. The resulting mixture was stirred for an additional 30 minutes under control with column chromatography (silical gel, $Cl_2CH_2$:MeOH 95:5). Afterwards, the phases were separated, the aqueous phase was extracted with toluene and the combined toluene phases were washed with water three times, dried over sodium sulfate, filtered and evaporated to dryness. 7 g (95.5%) of an oil were obtained, which solidified upon addition of a small amount of diethylether to yield a white amorphous solid that showed a crystalline transformation under melting at 130-133° C.

CCF($Cl_2CH_2$:MeOH 95:5):$R_f$=0.3

The analysis of the enantiomers via capillar electrophoresis gave 99.1% (S)-5-(4-chlorophenyl)-1-(2,4-dichlorophenyl)-4,5-dihydro-pyrazole-3-carboxylic acid 0.9% (R)-5-(4-chlorophenyl)-1-(2,4-dichlorophenyl)-4,5-dihydro-pyrazole-3-carboxylic acid Enantiomeric excess ee=98.2%

$[\alpha]_D$ (c=1.23° C., MeOH)=−480.5.

Chemical purity determined by HPLC: 99.1%

$^1$H-NMR (CDCl$_3$) δ ppm: 3.2 (dd, J=6.4 y 18.2 Hz, 1H), 3.7 (dd, J=12.7 y 18.2 Hz, 1H), 5.85 (dd, J=6.4 y 12.6 Hz, 1H), 7.0-7.2 (m, 7H).

Isolation of the Enantiomer (S)-5-(4-chlorophenyl)-1-(2,4-dichlorophenyl)-4,5-dihydro-pyrazole-3-carboxylic acid from the Mother Liquors Obtained from the Crystalisation of the Other Enantiomer (R)-5-(4-chlorophenyl)-1-(2,4-dichlorophenyl)-4,5-dihydro-pyrazole-3-carboxylic acid with (+)-cinchonine The residue obtained from the evaporation of the mother liquor obtained from the crystallisation of (R)-5-(4-chlorophenyl)-1-(2,4-dichlorophenyl)-4,5-dihydro-pyrazole-3-carboxylic acid with (+)-Cinchonine was treated with 6N HCl as described above for obtaining the free acid After evaporating the organic phase 23.63 g of a mixture with a theoretical composition of 13.34 mmoles of (R)-5-(4chlorophenyl)-1-(2,4-dichlorophenyl)-4,5-dihydro-pyrazole-3-carboxylic acid and 47.34 mmoles of (S)-5-(4-chlorophenyl)-1-(2,4-dichlorophenyl)-4,5-dihydro-pyrazole-3-carboxylic acid were obtained. Said mixture, dissolved in 118 ml of acetone, was added on top of a solution of 18.7 g (47.4 mmoles) of brucine in 650 ml of acetone, stirred for a couple of minutes and left to crystallize at room temperature overnight. A creme-coloured solid was obtained that was filtered off and dried to yield 28 g (77.5% relative to the (S)-salt).

Enantiomeric excess as determined by capilar electrophoresis was ee=98.2%

The purity of the isolated salt was comparable to the one of the salt obtained directly from the resolution of the racemate. Consequently, the same purification process as described above could be applied.

Preparation of (S)-N-piperidinyl-5-(4-chlorophenyl)-1-(2,4-dichlorophenyl)-4,5-dihydro-1H-pyrazole-3-carboxamide (A)

5.27 g (14.26 mmol) of (S)-5-(4-chlorophenyl)-1-(2,4-dichlorophenyl)-4,5-dihydro-pyrazole-3-carboxylic acid were dissolved in 30 ml of toluene, followed by the rapid dropwise addition of 1.25 ml (17.11 mmoles) of thionyl chloride and 7 drops of DMF. Under anhydrous nitrogen atmosphere the mixture was heated to a temperature of 75-80° C. under vigorous stirring for two hours and then allowed to cool to room temperature. Said acid chloride solution was then added dropwise to a solution of 1.84 ml (16-54 mmol) of N-Aminopiperidine, 8 ml (57 mmol) of triethylamine and 25 ml of anhydrous toluene, which was cooled to 0-5° C., thereby keeping the temperature below 10° C. during the addition. The reaction mixture was stirred at room temperature overnight, whereupon a suspension was obtained. Water and Toluene were added to said suspension until dissolution was complete and the phases were separated. The aqueous phase was extracted with toluene, the combined organic phases washed with an NaOH solution (10%) and water, dried over sodium sulfate, filtered off and evaporated to dryness to yield 6.85 g of an oil, which failed to crystallize using the solvents Ethanol, Ethylacetate and Acetone. The oil was purified via column chromatography over silica gel (eluent:petrol ether ethylacetate 90:10 to 50:50) to give 4.7 g (73%) of (S)-N-piperidinyl-5-(4-chlorophenyl)-1-(2,4-dichlorophenyl)-4,5-dihydro-1H-pyrazole-3-carboxamide in form of an amorphous solid of light yellow color (melting point 73-76° C.).

$^1$H-NMR (DMSO-d$_6$) δ ppm: 9.25 (s, 1H), 7.5 (d, J=8.8 Hz, 1H), 7.4 (d, J=2.3 Hz, 1H), 7.3-7.25 (2d, J=8.8 and 8.5 Hz, 3H), 7,1 (d, J=8.5 Hz, 2H), 5.8 (dd, J=5.7 and 11.8 Hz, 1 H), 3.65 (dd, J=1.8 and 18.1 Hz, 1H), 3.0 (dd, J=5.7 and 18.1 Hz, 1H), 2.75 (m, 4H). 1.5 (m, 4H), 1.2 (m, 2H).

Analysis of the enantiomer via chiral HPLC: ee=98%
Chemical purity determined by HPLC: 98.7%

Preparation of Hydrochloride salt of (S)-N-piperidinyl-5-(4-chlorophenyl)-1-(2,4-dichlorophenyl)-4,5-dihydro-1H-pyrazole-3-carboxamide (A-Hydrochloride)

0.2 g (0.4 mmol) of (S)-N-piperidinyl-5-(4-chlorophenyl)-1-(2,4dichlorophenyl)-4,5-dihydro-1H-pyrazole-3-carboxamide were dissolved in 3 ml isopropanol, cooled with ice and a saturated HCl-ethanol solution was added. The solution changed its color and a white solid formed, which was filtered off, washed with isopropanol:diethylether (1:1) and dried to yield 0.14 g (72%) of a white solid with a melting point of 165-175° C. The purity determined by HPLC was 99.3%. Determination of chlorine: 7.15% (98.5% of the theoretical value).

$^1$H-NMR (DMSO-$d_6$) δ ppm: 10.4 (bs, 1H), 7.45 (m, 2H), 7.3 (2d, J=2.6 y 8.5 Hz, 3H). 7.15 (d, J=8.5 Hz, 2H), 5.8 (dd, J=6.3 y 12.0 Hz, 1H), 3.7 (dd, J=12.0 y 18.0 Hz, 1H), 3.05 (m, 5H), 1.7 (m, 4H), 1.4 (m, 2H).

Pharmacological Data

The antagonism of the pyrazoline compounds of general formula I to the CB1-receptor was determined according to the method described in Pharmacological methods, part VI (table 1).

TABLE 1

| Compound according to example | Antagonism [%] |
|---|---|
| A | 43 |
| A-Hydrochloride | −7 |

The invention claimed is:

1. A 5-(S)-substituted pyrazoline compound of formula I

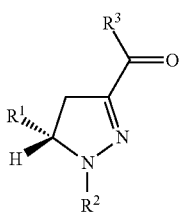

I wherein
  $R^1$ represents a phenyl group, which is optionally substituted by one or more substituents independently selected from the group consisting of methyl, ethyl, F, Cl, Br and $CF_3$,
  $R^2$ represents a phenyl group, which is optionally substituted by one or more substituents independently selected from the group consisting of methyl, ethyl, F, Cl, Br and $CF_3$,
  $R^3$ represents an —$NR^4R^5$-moiety,
  one of the residues $R^4$ and $R^5$ represents a hydrogen atom and the other one of these residues $R^4$ and $R^5$ represents an optionally at least mono-substituted pyrrolidinyl group; an optionally at least mono-substituted piperidinyl group; an optionally at least mono-substituted piperazinyl group; an optionally at least mono-substituted triazolyl group; an —$SO_2$—$R^6$-moiety; or an —$NR^7R^8$-moiety, or $R^4$ and $R^5$, identical or different, represent a methyl group, an ethyl group, an n-propyl group, an isopropyl group, an n-butyl group, a sec-butyl group or a tert-butyl group,
  $R^6$ represents a $C_{1-6}$-alkyl group; a saturated, optionally at least mono-substituted cycloaliphatic group, which may be condensed with a mono- or polycyclic ring-system; or a phenyl group, which is optionally substituted with one or more $C_{1-6}$ alkyl groups, and
  $R^7$ and $R^8$, identical or different, represent a hydrogen atom or a $C_{1-6}$ alkyl radical
  optionally in form of a corresponding N-oxide thereof, or a corresponding salt thereof.

2. A 5-(S)-substituted pyrazoline compound of formula I

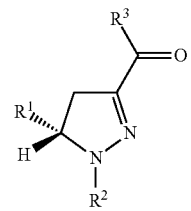

I wherein
  $R^1$ represents a phenyl group, which is optionally substituted with 1, 2, 3, 4 or 5 substituents independently selected from the group consisting of methyl, ethyl, F, Cl, Br and $CF_3$,
  $R^2$ represents a phenyl group, which is optionally substituted with 1, 2, 3, 4 or 5 substituents independently selected from the group consisting of methyl, ethyl, F, Cl, Br and $CF_3$,
  $R^3$ represents an —$NR^4R^5$-moiety,
  $R^4$ represents a hydrogen atom or a linear or branched $C_{1-6}$-alkyl group,
  $R^5$ represents a linear or branched $C_{1-6}$-alkyl group; an —$SO_2$—$R^6$-moiety; a pyrrolidinyl group; a piperidinyl group; a piperazinyl group; a homo-piperazinyl group; a morpholinyl group; a triazolyl group; whereby each of the heterocyclic rings may be substituted with one or more, identical or different, $C_{1-6}$-alkyl groups, and
  $R^6$ represents a phenyl group, which is optionally substituted with one or more $C_{1-6}$ alkyl groups, which may be identical or different,
  optionally in form of a corresponding N-oxide thereof, or a corresponding salt thereof.

3. A 5-(S)-substituted pyrazoline compound of formula I

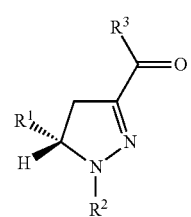

I wherein
  $R^1$ represents a phenyl ring, which is mono-substituted with a halogen atom,
  $R^2$ represents a phenyl ring, which is di-substituted with two halogen atoms,
  $R^3$ represents an —$NR^4R^5$-moiety,
  $R^4$ represents a hydrogen atom or a linear or branched $C_{1-6}$-alkyl group,
  $R^5$ represents a linear or branched $C_{1-6}$ alkyl group; an —$SO_2$—$R^6$-moiety; a pyrrolidinyl group; a piperidinyl group; a piperazinyl group, a homo-piperazinyl group; a morpholinyl group; or a triazolyl group whereby each of the heterocyclic rings may be substituted with one or more, identical or different, $C_{1-6}$-alkyl groups, and $R^6$ represents a phenyl group, which is optionally substituted with one or more $C_{1-6}$ alkyl groups, which may be identical or different, optionally in form of a corresponding N-oxide thereof, or a corresponding salt thereof.

4. The 5-(S)-substituted pyrazoline compound (S)-N-piperidinyl-5-(4-chloro-phenyl)-1-(2,4-dichlorophenyl)-4,5-dihydro-1H-pyrazol-3-carboxamide according to claim 1:

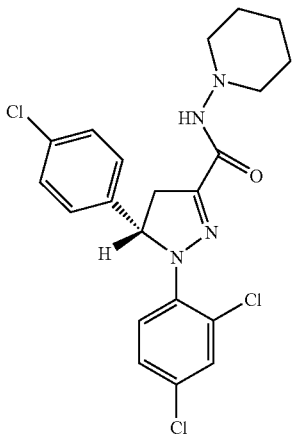

optionally in the form of a corresponding N-oxide, or a corresponding salt.

5. A process for the manufacture of substituted pyrazoline compounds of formula I according to claim 1, characterized in that at least one compound of formula IIa

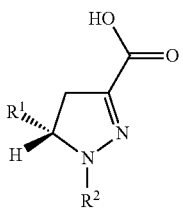
(IIa)

wherein $R^1$ and $R^2$ have the meaning according to claim 1, is optionally transferred under inert atmosphere to a compound of formula (III) via reaction with an activating agent

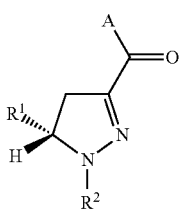
(III)

wherein the substituents $R^1$ and $R^2$ have the meaning given above and A represents a leaving group, said compound being optionally isolated or optionally purified, and at least one compound of formula (IIa) is reacted with a compound of formula $R^3H$, wherein $R^3$ represents an —$NR^4R^5$-moiety, with $R^4$ and $R^5$ having the meaning according to claim 1, under inert atmosphere to yield a substituted pyrazoline compound of formula I, wherein $R^3$ represents an —$NR_4R_5$-moiety, or at least one compound of formula (III) is reacted with a compound of the formula $R^3H$, in which $R^3$ has the meaning according to claim 1 under inert atmosphere to yield a compound of formula (I) according to claim 1 which is optionally isolated or optionally purified.

6. A process according to claim 5, wherein the compound IIa is obtained from a mixture comprising the enantiomers

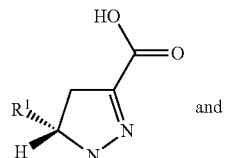
(IIa)

and

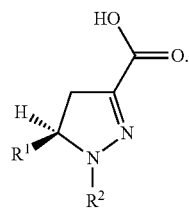
(IIb)

7. A process according to claim 6, wherein the compound IIa is obtained from the mixture in form of an addition compound with a chiral base.

8. A process according to claim 6, wherein the mixture comprising the enantiomers IIa and IIb is obtained by reacting at least one benzaldehyde compound of formula IV

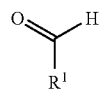
(IV)

with a pyruvate compound of formula (V)

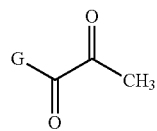
(V)

wherein G represents an OR group with R being a branched or unbranched $C_{1-6}$ alkyl radical or G represents an O⁻ K group with K being a cation, to yield a compound of formula (VI)

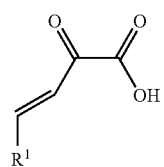
(VI)

wherein $R^1$ has the meaning given above, which is optionally isolated or optionally purified, and which is reacted with an optionally substituted phenyl hydrazine of formula (VII)

 (VII)

or a corresponding salt thereof, under inert atmosphere, to yield a mixture of compounds

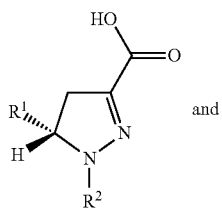 (IIa)

and

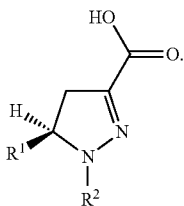 (IIb)

9. A medicament comprising one or more substituted pyrazoline compounds of formula I according to claim 1, and one or more pharmaceutically acceptable excipients.

10. A compound according to claim 3, wherein $R^1$ represents a phenyl ring, which is mono-substituted with a chlorine atom, in its 4-position.

11. A compound according to claim 3, wherein $R^2$ represents a phenyl ring, which is di-substituted with two chlorine atoms, in its 2- and 4-position.

* * * * *